United States Patent [19]
Pecker et al.

[11] Patent Number: 5,968,822
[45] Date of Patent: Oct. 19, 1999

[54] POLYNUCLEOTIDE ENCODING A POLYPEPTIDE HAVING HEPARANASE ACTIVITY AND EXPRESSION OF SAME IN TRANSDUCED CELLS

[76] Inventors: Iris Pecker, 42 Wolfson, Rishon le Zion 75203; Israel Vlodavsky, 34 Arbel, Mevaseret Zion 90805; Elena Feinstein, 12/29 Hahagana, Rehovot 76214, all of Israel

[21] Appl. No.: 08/922,170

[22] Filed: Sep. 2, 1997

[51] Int. Cl.$^6$ ............................. C12N 15/56; C12N 5/10; C12N 15/63; C12N 9/24
[52] U.S. Cl. ........................ 435/325; 536/23.1; 536/23.2; 435/320.1; 435/252.3; 435/200
[58] Field of Search ................................ 536/23.1, 23.2; 435/320.1, 252.3, 325, 348, 200

[56] References Cited

U.S. PATENT DOCUMENTS

5,362,641  11/1994  Fuks et al. ............................... 435/209
5,571,506  11/1996  Regan et al. .......................... 424/78.17

FOREIGN PATENT DOCUMENTS

WO 9504518  7/1994  WIPO .

OTHER PUBLICATIONS

Goshen et al, "Purification and Characterization of Placental Heparanase and its Expression by Cultured Cytotrophoblats", *Molecular Huiman Reproduction*, 2(9): 679–684, 1996.

Bar–Ner et al, "Inhibition of Heparanase–Mediated Degradatin of Extracellular Matrix Heparan Sulphate by Non–anticoagulant Heparin Species", *Blood*, 70(2): 551–557, 1987.

Savitsky et al, "Ataxia–Telangiectasia: Structural Diversity of Untranslated Sequences Suggests Complex Post–Transcriptional Regulation of ATM Gene Expression", *Nucleic Acids Research*, 25(9): 1678–1684 (1997).

Haimovitz–Friedman et al, "Activation of Platelet Heparitanase by Tumor Cell–Derived Factors", *Blood*, 78: 789–796, 1991.

Gospodarowicz et al, Stimulation of Corneal Endothelial Cell Proliferation in vitro by Fibroblast and Epidemal Growth Factors, *Exp. Eye Res.*, 25: 75–89, 1977.

Ernst et al, "Enzymsatic degradation of Glycosaminoglycans", *Crit. Rev. In Biochem. & Molec. Biology*, 30(5): 387–444, 1995.

Zhong–Sheng et al, "Role of Heparan Sulfate Proteoglycans in the Binding and Uptake of Apoliprotein E–enriched Remnant Lipoproteins by Cultured Cells", *J. Biol. Chem.*, 268(14): 10160–10167, 1993.

R. Ross, "The Pathogenesis of Atheroscerosis: A Perspective for the 1990s", *Nature*, 362: 801–809, (1993).

1993 Putnak et al, "A Putative Cellular Receptor for Dengue Viruses", *Nature Medicine*, 3(8): 828–829, 1997.

Cordon–Cardo et al, "Expression of Basic Fibroblast Growth Factor in Normal Human Tissues", *Laboratory Investigation*, 63(6): 832–840, 1990.

Narindrasorasak et al, "High Affinity Interactions between the Alzheimer's β–Amyloid Precursor Proteins and the Basement Membrane Form of Heparan Sulfate Proteoglycan", *J. Biol. Chem.*, 266 (20): 12878–12883, 1991.

Chen et al, "Dengue Virus Infectivity Depends opn Envelope Proteion Bin to Target Cell Heparan Sulfate", *Nature Medicine*, 3(8): 866–871, 1997.

Shieh et al, "Cell Surface Receptors for Herpes Simplex Virus are Heparan Sulfate Proteoglycan Proteoglycans", *J. Cell Biol.*, 116(5): 1273–1281, 1992.

Eisenberg et al, "Liposprotein Lipase Enhances Binding of Lipoproteins to Heparan Sulfate on Cell Surfaces and Extracellular Matrix", *J. Clin. Invest.*, 90: 2013–2021, 1992.

Rapraeger et al, "Requirement of Heparan Sulfate for bFG-F–Mediated Fibroblast Growth and Myoblast Differentiation", *Science*, 252: 1705–1708, 1991.

Lider et al, "A Disaccharide that Inhibits Tumor Necrosis Factor α is Formed from the Extracellular Matrix by the Enzyme Heparanase", *Proc. Natl. Acad. Sci. USA*, 92:5037–5041, 1995.

Lider et al, "Suppression of Experimental Autoimmune Diseases and Prolongation of Allograft Survival by Treatment of Animals with Low Doses of Heparins", *J. Clin. Invest.*, 83: 752–756, 1989.

Gitay–Goren et al, "The Binding of Vascular Endothelial Growth Factor to its Receptors is Dependent on Cell Surface–associated Heparin–like Molecules", *J. Biol. Chem.*, 267(9): 6093–6098, 1992.

Ornitz et al, "FGF Binding and FGF Receptor Activation by Synthetic Heparin Derived Di–and Trisaccharides", *Science*, 268: 432–436, 1995.

Spivak–Kroizman et al, "Heparin–Induced Oligomerization of FGF Molecules is Responsible for FGF Receptor Dimerization, Activation, and Cell Proliferation", *Cell*, 79: 1015–1024, 1994.

Yayon et al, "Cell Surface, Heparin–Like Molecules are required for Binding of Basic Fibroblast Growth Factor to its High Affinity Receptor", *Cell*, 64: 841–848, 1991.

Vlodavsky et al, "Extracellular Matrix–Bound Growth Factors, Enzymes, and Plasma Proteins", Basic Membranes: Cellular and Molecular Aspects (eds. Rohrbach & Timpl) pp. 327–343, Academic Press, Orlasndo, Fla., 1993.

Vlodavsky et al, "Extracellular Sequestration and release of Fibroblast Growth Factor: A Regulatory Mechanism?", *Trends Biochem. Sci.*, 16: 268–271, 1991.

Ishai–Michaeli et al, "Heparanase Activity Expressed by Platelets, Neutrophils, and Lymphoma Cells releases Active Fibroblast Growth Factor from ExtraCellular Matrix", *Cell Regulation*, 1: 833–842, 1990.

(List continued on next page.)

*Primary Examiner*—Rebecca E. Prouty
*Attorney, Agent, or Firm*—Mark M. Friedman

[57] ABSTRACT

A polynucleotide (hpa) encoding a polypeptide having heparanase activity, vectors including same, transduced cells expressing heparanase and a recombinant protein having heparanase activity.

30 Claims, 13 Drawing Sheets

OTHER PUBLICATIONS

Ishai–Michaeli et al, "Importance of Size and Sulfatiuon of Heparin in Release of Basic Fibroblast Growth Factor from the Vascular Endothelium and ExtraCellular Matrix", *Biochemistry*, 31(7): 2080–2088, 1992.

Folkman et al, "Heparin–Binding Angiogenic Protein—Basic Fibroblast Growth Factor—is Stored Within Basement Membrane", *Am. J. Pathology*, 130(2): 393–400, 1988.

Vlodavsky et al, "Endothelial Cell–Derived Basic Fibroblast Growth Factor: Synthesis and Deposition into Subendothelial ExtraCellular Matrix", *Proc. Natl. Acad. Sci. USA*, 84: 2292–2296, 1987.

Folkman et al, "Angiogenic Factors", *Science*, 235: 442–447, 1987.

Burgess et al, "The Heparin–Binding (Fibroblast) Growth Factor Family of Proteins", *Annu. Rev. Biochem.*, 58:575–606, 1989.

Vlodavsky et al, "Involvement of the ExtraCellular Matrix, Heparin Sulfate Proteoglycans, and Heparin Sulfate Degrading Enzymes in Angiogenesis and Metastis", In: *Tumor Angeogenesis*, Eds. Lewis et al, Oxford Univ. Press, pp. 125–140, 1997.

Parish et al, "Evidence that Sulfated Polysaccharides Inhibit Tumor Metastis by Blocking Tumor–Cell–Derived Heparanases", *Int. J. Cancer*, 40: 511–518, 1987.

Bashkin et al, "Basic Fibroblast Growth Factor Binds to Subendothlial ExtraCellular Matrix and is Released by Heparitanase and Heparin–Like Molecules", *Biochemistry*, 28:1737–1743, 1989.

Gospodarowicz et al, "Permissive effect of the ExtraCellular Matrix on Cell Proliferation in vitro", *Proc. Natl. Acad. Sci. USA*, 77(7): 4094–4098, 1980.

Vlodavsky et al, "Morphological Appearance, Growth Bhavior and Migratory Activity of Human Tumor Cells Maintained on ExtraCellular Matrix Versus Plastic", *Cell*, 19: 607–616, 1980.

Vlodavsky et al, "Involvement of Heparanase in Tumor Metastis and Angiogenesis", *Israel J. Med. Sci.*, 24: 464–470, 1988.

Vlodavsky et al, "Lymphoma Cell–nediated Degradation of Sulfated Proteoglycans in the Subendothelial ExtraCellular Matrix: Relationship to Tumor Cell Metastis", *Cancer Research*, 43: 2704–2711, 1983.

Liotta et al, "Tumor Invasion and the ExtraCellular Matrix", *Lab. Inv.*, 49(6): 636–649, 1983.

Nicolson, G.L., "Organ Specificity of Tumor Metastis: Role of Preferential Adhesion, invasion and growth of Malignant Cells at Specific Secondary Sites", *Cancer Met. Rev.*, 7: 143–188, 1988.

Nakajima et al, "Heparanases and Tumor Metastis", *J. Cell. Biochem.*, 36: 157–167, 1988.

Vlodavsky et al, "Inhibition of Tumor Metastis Inhibiting Species of Heparin", *Inv. Metast.*, 14: 290–302, 1994.

Vlodavsky et al, "Expression of Heparanases by Platelets and Circulating Cells of the Immune System: Possible Involvement in Diapedesis and Extravasation", *Inv. Metast*, 12: 112–127, 1992.

Ruoslahti et al, "Proteoglycans as Modulators of Growth Factor Activities", *Cell*, 64: 867–869, 1991.

Kjellen et al, "Proteoglycans: Structures and Interactions", *Annu. Rev. Biochem.*, 60: 443–475, 1991.

Wight, T.N., "Cell Biology of Arterial Proteoglycans", *Arteriosclerosis*, 9: 1–20, 1989.

Jackson, et al, "Glycosaminoglycans: Molecular Properties, Protein Interactions, and Role in Phsiological Processes", *Physiological Rev.*, 71(2): 481–539, 1991.

Wight et al, "The Role of Proteoglycans in Cell Adhesion, Migration and Proliferation", *Curr. Opin. Cell Biol.*, 4: 793–801, 1992.

FIG. 1

```
   1 CTAGAGCTTTCGACTCTCCGCTGCGCGGCAGCTGGCGGGGGGAGCAGCCAGGTGAGCCCA

61 AGATGCTGCTGCGCTCGAAGCCTGCGCTGCCGCCGCCGCTGATGCTGCTGCTCCTGGGGC
      M  L  L  R  S  K  P  A  L  P  P  P  L  M  L  L  L  L  G  P

121 CGCTGGGTCCCCTCTCCCCTGGCGCCCTGCCCCGACCTGCGCAAGCACAGGACGTCGTGG
      L  G  P  L  S  P  G  A  L  P  R  P  A  Q  A  Q  D  V  V  D

181 ACCTGGACTTCTTCACCCAGGAGCCGCTGCACCTGGTGAGCCCCTCGTTCCTGTCCGTCA
      L  D  F  F  T  Q  E  P  L  H  L  V  S  P  S  F  L  S  V  T

241 CCATTGACGCCAACCTGGCCACGGACCCGCGGTTCCTCATCCTCCTGGGTTCTCCAAAGC
      I  D  A  N  L  A  T  D  P  R  F  L  I  L  L  G  S  P  K  L

301 TTCGTACCTTGGCCAGAGGCTTGTCTCCTGCGTACCTGAGGTTTGGTGGCACCAAGACAG
      R  T  L  A  R  G  L  S  P  A  Y  L  R  F  G  G  T  K  T  D

361 ACTTCCTAATTTTCGATCCCAAGAAGGAATCAACCTTTGAAGAGAGAAGTTACTGGCAAT
      F  L  I  F  D  P  K  K  E  S  T  F  E  E  R  S  Y  W  Q  S

421 CTCAAGTCAACCAGGATATTTGCAAATATGGATCCATCCCTCCTGATGTGGAGGAGAAGT
      Q  V  N  Q  D  I  C  K  Y  G  S  I  P  P  D  V  E  E  K  L

481 TACGGTTGGAATGGCCCTACCAGGAGCAATTGCTACTCCGAGAACACTACCAGAAAAAGT
      R  L  E  W  P  Y  Q  E  Q  L  L  R  E  H  Y  Q  K  K  F

541 TCAAGAACAGCACCTACTCAAGAAGCTCTGTAGATGTGCTATACACTTTTGCAAACTGCT
      K  N  S  T  Y  S  R  S  S  V  D  V  L  Y  T  F  A  N  C  S

601 CAGGAATGGACTTGATCTTTGGCCTAAATGCGTTATTAAGAACAGCAGATTTGCAGTGGA
      G  I  D  L  I  F  G  L  N  A  L  L  R  T  A  D  L  Q  W  N

661 ACAGTTCTAATGCTCAGTTGCTCCTGGACTACTGCTCTTCCAAGGGGTATAACATTTCTT
      S  S  N  A  Q  L  L  L  D  Y  C  S  S  K  G  Y  N  I  S  W

721 GGGAACTAGGCAATGAACCTAACAGTTTCCTTAAGAAGGCTGATATTTTCATCAATGGGT
      E  L  G  N  E  P  N  S  F  L  K  K  A  D  I  F  I  N  G  S
                 (T)

781 CGCCAGTTAGGAGAAGATTATATTCAATTGCATAAACTTCTAAGAAAGTCCACCTTCAAA
      Q  L  G  E  D  Y  I  Q  L  E  K  L  L  R  K  S  T  F  K  N
                                                             (F)

841 ATGCAAAACTCTATGGTCCTGATGTTGGTCAGCCTCGAAGAAAGACGGCTAAGATGCTGA
      A  K  L  Y  G  P  D  V  G  Q  P  R  R  K  T  A  K  M  L  K

901 AGAGCTTCCTGAAGGCTGGTGGAGAAGTGATTGATTCAGTTACATGGCATCACTACTATT
      S  F  L  K  A  G  G  E  V  I  D  S  V  T  W  H  Y  Y  L

961 TGAATGGACGGACTGCTACCAGGGAAGATTTTCTAAACCCTGATGTATTGGACATTTTTA
      N  G  R  T  A  T  R  E  D  F  L  N  P  D  V  L  D  I  F  I

1021 TTTCATCTGTGCAAAAAGTTTTCCAGGTGGTTGAGAGCACCAGGCCTGGCAAGAAGGTCT
      S  S  V  Q  K  V  F  Q  V  V  E  S  T  R  P  G  K  K  V  W

1081 GGTTAGGAGAAACAAGCTCTGCATATGGAGGCGGAGCGCCCTTGCTATCCGACACCTTTG
      L  G  E  T  S  S  A  Y  G  G  G  A  P  L  L  S  D  T  F  A

1141 CAGCTGGCTTTATGTGGCTGGATAAAATTGGGCCTGTCAGCCCGAATGGGAATAGAAGTGG
      A  G  F  M  W  L  D  K  L  G  L  S  A  R  M  G  I  E  V  V

1201 TGATGAGGCAAGTATTCTTTGGAGCAGGAAACTACCATTTAGTGGATGAAAACTTCGATC
      M  R  Q  V  F  F  G  A  G  N  Y  H  L  V  D  E  N  F  D  P

1261 CTTTACCTGATTATTGGCTATCTCTTCTGTTCAAGAAATTGGTGGGCACCAAGGTGTTAA
      L  P  D  Y  W  L  S  L  L  F  K  K  L  V  G  T  K  V  L  M

1321 TGGCAAGCGTGCAAGGTTCAAAGAGAAGGAAGCTTCGAGTATACCTTCATTGCACAAACA
      A  S  V  Q  G  S  K  R  R  K  L  R  V  Y  L  H  C  T  N  T

1381 CTGACAATCCAAGGTATAAAGAAGGAGATTTAACTCTGTATGCCATAAACCTCCATAACG
      D  N  P  R  Y  K  E  G  D  L  T  L  Y  A  I  N  L  H  N  V

1441 TCACCAAGTACTTGCGGTTACCCTATCCTTTTTCTAACAAGCAAGTGGATAAATACCTTC
      T  K  Y  L  R  L  P  Y  P  F  S  N  K  Q  V  D  K  Y  L  L

1501 TAAGACCTTTGGGACCTCATGGATTACTTTCCAAATCTGTCCAACTCAATGGTCTAACTC
      R  P  L  G  P  H  G  L  L  S  K  S  V  Q  L  N  G  L  T  L

1561 TAAAGATGGTGGATGATCAAACCTTGCCACCTTTAATGGAAAAACCTCTCCGGCCAGGAA
      K  M  V  D  D  Q  T  L  P  P  L  M  E  K  P  L  R  P  G  S

1621 GTTTACTGGGCTTGCCAGCTTTCTCCATATAGTTTTTTTGTGATAAGAAATGCCAAAGTTG
      S  L  G  L  P  A  F  S  Y  S  F  F  V  I  P  N  A  K  V  A
```

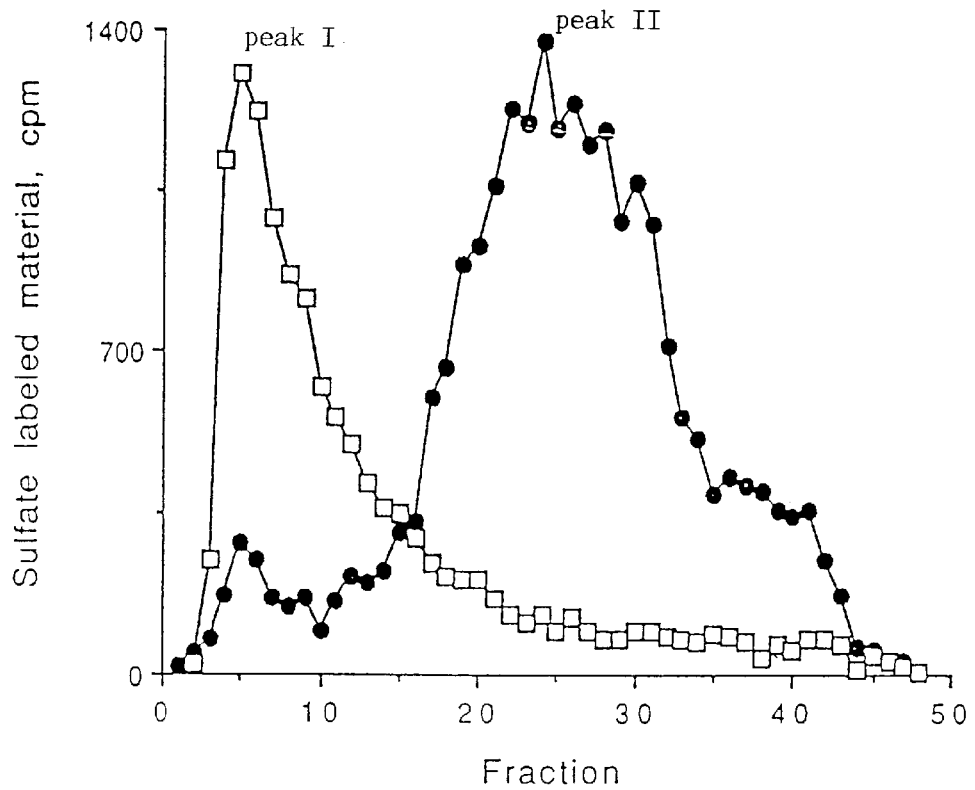
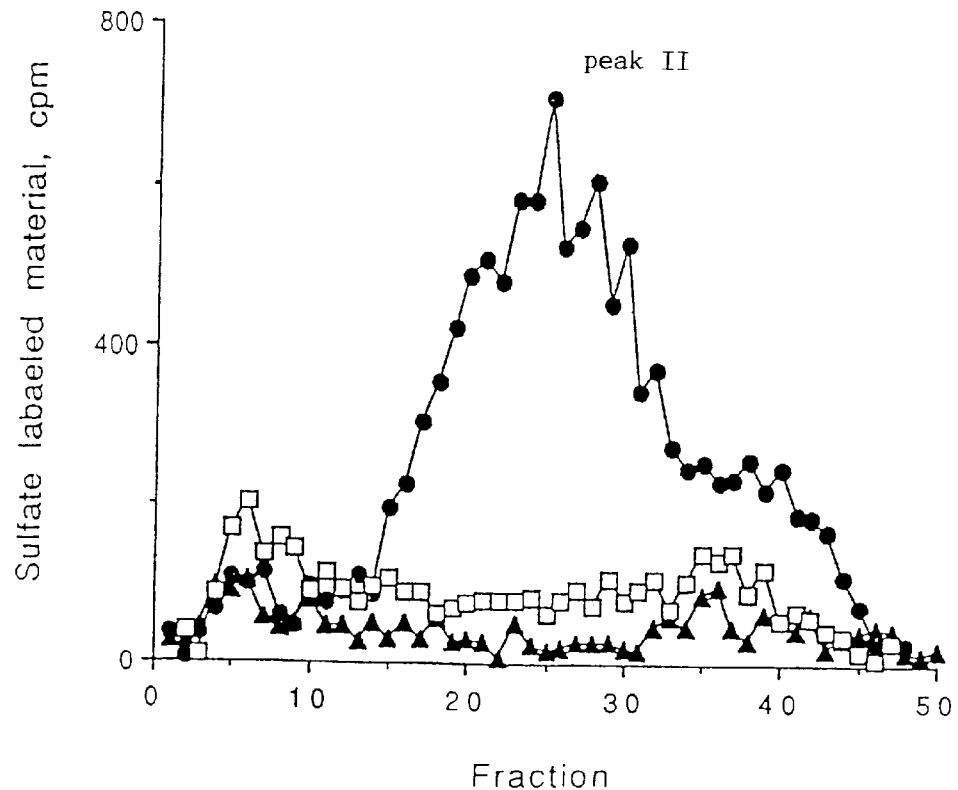

Fig 13

```
mouse  CTGGCAAGAAGGTCTGGTTGGGAGAGACGAGCTCAGCTTACGGTGGCGGT 50
       ||||||||||||||||||| ||||| || |||||| || || || |||||
human  CTGGCAAGAAGGTCTGGTTAGGAGAAACAAGCTCTGCATATGGAGGCGGA 1115 mouse  GCACCCTTGCTGTCCAACACCTTTGCAGCTGGCTTTATGTGGCTGGATAA 100
       || |||||||| ||| ||||||||||||||||||||||||||||||||||
human  GCGCCCTTGCTATCCGACACCTTTGCAGCTGGCTTTATGTGGCTGGATAA 1165 mouse  ATTGGGCCTGTCAGCCCAGATGGGCATAGAAGTCGTGATGAGGCAGGTGT 150
       |||||||||||||||||| ||||| |||||||| ||||||||||| || |
human  ATTGGGCCTGTCAGCCCGAATGGGAATAGAAGTGGTGATGAGGCAAGTAT 1215 mouse  TCTTCGGAGCAGGCAACTACCACTTAGTGGATGAAAACTTTGAGCCTTTA 200
       |||| ||||||||| |||||||| |||||||||||||||| || ||||||
human  TCTTTGGAGCAGGAAACTACCATTTAGTGGATGAAAACTTCGATCCTTTA 1265 mouse  CCTGATTACTGGCTCTCTCTTCTGTTCAAGAAACTGGTAGGTCCCAGGGT 250
       |||||||| ||||| |||||||||||||||||| ||||| || ||| |||
human  CCTGATTATTGGCTATCTCTTCTGTTCAAGAAATTGGTGGGCACCAAGGT 1315 mouse  GTTACTGTCAAGAGTGAAAGGCCCAGACAGGAGCAAACTCCGAGTGTATC 300
       |||| || |||| ||| |||| || | || || || || ||||| || |
human  GTTAATGGCAAGCGTGCAAGGTTCAAAGAGAAGGAAGCTTCGAGTATACC 1365 mouse  TCCACTGCACTAACGTCTATCACCCACGATATCAGGAAGGAGATCTAACT 350
       | || |||||| |||    |  ||| | ||| | |||||||||  |||||
human  TTCATTGCACAAACACTGACAATCCAAGGTATAAAGAAGGAGATTTAACT 1415 mouse  CTGTATGTCCTGAACCTCCATAATGTCACCAAGCACTTGAAGGTACCGCC 400
       ||||||| | | |||||||||||| |||||||||| ||||  |||||| |
human  CTGTATGCCATAAACCTCCATAACGTCACCAAGTACTTGCGGTTACCCTA 1465 mouse  TCCGTTGTTCAGGAAACCAGTGGATACGTACCTTCTGAAGCCTTCGGGGC 450
       ||| || |  | ||  || ||| |||| | ||||||| |||| |  ||| |
human  TCCTTTTTCTAACAAGCAAGTGGATAAATACCTTCTAAGACCTTTGGGAC 1515 mouse  CGGATGGATTACTTTCCAAATCTGTCCAACTGAACGGTCAAATTCTGAAG 500
       |  |||||||||||||||||||||||||||||| ||||| || || |||
human  CTCATGGATTACTTTCCAAATCTGTCCAACTCAATGGTCTAACTCTAAAG 1565 mouse  ATGGTGGATGAGCAGACCCTGCCAGCTTTGACAGAAAAACGTCTCCCCGC 550
       ||||||||| || || ||||| |||| | |||||||||| |||||||| |
human  ATGGTGGATGATCAAACCTTGCCACCTTTAATGGAAAAACCTCTCCGGCC 1615 mouse  AGGAAGTGCACTAAGCCTGCCTGCCTTTTCCTATGGTTTTTTTGTCATAA 600
       ||||||| |||| ||  |||| || || || ||| |||||||||| ||||
human  AGGAAGTTCACTGGGCTTGCCAGCTTTCTCATATAGTTTTTTTGTGATAA 1665 mouse  GAAATGCCAAAATCGCTGCTTGTATATGAAAATAAAA 637
       |||||||||| | ||||||||| |||  ||||||||
human  GAAATGCCAAAGTTGCTGCTTGCATCTGAAAATAAAA 1702
```

POLYNUCLEOTIDE ENCODING A POLYPEPTIDE HAVING HEPARANASE ACTIVITY AND EXPRESSION OF SAME IN TRANSDUCED CELLS

FIELD AND BACKGROUND OF THE INVENTION

The present invention relates to a polynucleotide, referred to hereinbelow as hpa encoding a polypeptide having heparanase activity vectors including same and transduced cells expressing heparanase. The invention further relates to a recombinant protein having heparanase activity.

Heparan sulfate proteoglycans: Heparan sulfate proteoglycans (HSPG) are ubiquitous macromolecules associated with the cell surface and extra cellular matrix (ECM) of a wide range of cells of vertebrate and invertebrate tissues (1–4). The basic HSPG structure includes a protein core to which several linear heparan sulfate chains are covalently attached. These polysaccharide chains are typically composed of repeating hexuronic and D-glucosamine disaccharide units that are substituted to a varying extent with N- and O-linked sulfate moieties and N-linked acetyl groups (1–4). Studies on the involvement of ECM molecules in cell attachment, growth and differentiation revealed a central role of HSPG in embryonic morphogenesis, angiogenesis, neurite outgrowth and tissue repair (1–5). HSPG are prominent components of blood vessels (3). In large blood vessels they are concentrated mostly in the intima and inner media whereas in capillaries they are bound mainly in the subendothelial basement membrane where they support proliferating and migrating endothelial cells and stabilize the structure of the capillary wall. The ability of HSPG to interact with ECM macromolecules such as collagen, laminin and fibronectin, and with different attachment sites on plasma membranes suggests a key role for this proteoglycan in the self-assembly and insolubility of ECM components as well as in cell adhesion and locomotion. Cleavage of the heparan sulfate (HS) chains may therefore result in degradation of the subendothelial ECM and hence may play a decisive role in extravasation of blood-borne cells. HS catabolism is observed in inflammation, wound repair. diabetes, and cancer metastasis, suggesting that enzymes which degrade HS play important roles in pathologic processes. Heparanase activity has been described in activated immune system cells and highly metastatic cancer cells (6–8), but research has been handicapped by the lack of biologic tools to explore potential causative roles of heparanase in disease conditions.

Involvement of Heparanase in Tumor Cell In vasion and Metastasis: Circulating tumor cells arrested in the capillary beds of different organs must invade the endothelial cell lining and degrade its underlying basement membrane (BM) in order to invade into the extravascular tissue(s) where they establish metastasis (9, 10). Metastatic tumor cells often attach at or near the intercellular junctions between adjacent endothelial cells. Such attachment of the metastatic cells is followed by rupture of the junctions. retraction of the endothelial cell borders and migration through the breach in the endothelium toward the exposed underlying BM (9). Once located between endothelial cells and the BM, the invading cells must degrade the subendothelial glycoproteins and proteoglycans of the BM in order to migrate out of the vascular compartment. Several cellular enzymes (e.g., collagenase IV, plasminogen activator, cathepsin B, elastase, etc.) are thought to be involved in degradation of BM (10). Among these enzymes is an enido-β-D-glucuronidase (heparanase) that cleaves HS at specific intrachain sites (6, 8, 11). Expression of a HS degrading heparanase was found to correlate with the metastatic potential of mouse lymphlomiia (11). Fibrosarcoma and melanoma (8) cells. Moreover, elevated levels of heparanase were detected in sera from metastatic tumor bearing animals and melanoma patients (8) and in tumor biopsies of cancer patients (12).

The control of cell proliferation and tumor progression by the local microenvironment, focusing on the interaction of cells with the extracellular matrix (FCM) produced by cultured corneal and vascular endothelial cells, was investigated previously by the present inventors. This cultured ECM closely resembles the subendothelium in vivo in its morphological appearance and molecular composition. It contains collagens (mostly type III and IV, with smaller amounts of types I and V), proteoglycans (mostly heparan sulfate- and dermatan sulfate-proteoglycans, with smaller amounts of chondroitin sulfate proteoglycans), laminin, fibronectin, entactin and elastin (13. 14). Tic ability of cells to degrade HS in the cultured ECM was studied by allowing cells to interact with a metabolically sulfate labeled ECM, followed by gel filtration (Sepharose 6B) analysis of degradation products released into the culture medium (11). While intact HSPG are eluted next to the void volume of the column ($K_{av}<0.2$, $M_r\sim 0.5\times 10^6$), labeled degradation fragments of HS side chains are eluted more toward the $V_t$ of the column ($0.5<k_{av}<0.8$, $M_r=5-7\times 10^3$) (11).

The heparanase inhibitory effect of various non-anticoagulant species of heparin that might be of potential use in preventing extravasation of blood-borne cells was also investigated by the present inventors. Inhibition of heparanase was best achieved by heparin species containing 16 sugar units or more and having sulfate groups at both the N and O positions. While O-desulfation abolished the heparanase inhibiting effect of heparin, O-sulfated, N-acetylated heparin retained a high inhibitory activity, provided that the N-substituted molecules had a molecular size of about 4,000 daltons or more (7). Treatment of experimental animals with heparanase inhibitors (e.g., non-anticoagulant species of heparin) markedly reduced (>90%) the incidence of lung metastases induced by B16 melanoma Lewis lung carcinoma and mammary adenocarcinoma cells (7, 8, 16). Heparin fractions with high and low affinity to anti-thrombin III exhibited a comparable high anti-metastatic activity, indicating that the heparaniase inhibiting activity of heparin, rather than its anticoagulant activity, plays a role in the anti-metastatic properties of the polysaccharide (7).

Heparanase activity in the urine of cancer patients: In an attempt to further elucidate the involvement of heparanase in tumor progression and its relevance to human cancer, urine samples for heparaniase activity were screened (16a). Heparanase activity was detected in the urine of some, but not all, cancer patients. High levels of heparanase activity were determined in the urine of patients with an aggressive metastatic disease and there was no detectable activity in the urine of healthy donors.

Heparanase activity was also found in the urine of 20% of normal and microalbuminuric insulin dependent diabetes mellitus (IDDM) patients, most likely due to diabetic nephropathy, the most important single disorder leading to renal failure in adults.

Possible involvement of heparanase in tumor angiogenesis: Fibroblast growth factors are a family of structurally related polypeptides characterized by high affinity to heparin (17). They are highly mitogenic for vascular endothelial cells and are among the most potent inducers of neovascularization (17, 18). Basic fibroblast growth factor (bFGF) has been extracted from the subendothelial ECM produced in vitro (19) and from basement membranes of the cornea (20). suggesting that ECM may serve as a reservoir for bFGF. Immunohistochemical staining revealed the localization of bFGF in basement membranes of diverse tissues and blood vessels (21). Despite the ubiquitous presence of bFGF in normal tissues endothelial cell proliferation in these tissues is usually very low, suggesting that bFGF is somehow sequestered from its site of action. Studies on the interaction of bFGF with ECM revealed that bFGF binds to HSPG in the ECM and can be released in an active form by HS degrading enzymes (15, 20, 22). It was demonstrated that heparanase activity expressed by platelets mast cells, neutrophils and lymphoma cells is involved in release of active bFGF from ECM and basement membranes (23), suggesting that heparanase activity may not only function in cell migration and invasion, but may also elicit an indirect neovascular response. These results suggest that the FCM HSPG provides a natural storage depot for bFGF and possibly other heparin-binding growth promoting factors (24, 25). Displacement of bFGF from its storage within basement membranes and ECM may therefore provide a novel mechanism for induction of neovascularization in normal and pathological situations.

Recent studies indicate that heparin and HS are involved in binding of bFGF to high affinity cell surface receptors and in bFGF cell signaling (26, 27). Moreover, the size of HS required for optimal effect was similar to that of HS fragments released by heparanase (28). Similar results were obtained with vascular endothelial cells growth factor (VEGF) (29), suggesting the operation of a dual receptor mechanism involving HS in cell interaction with heparin-binding growth factors. It is therefore proposed that restriction of endothelial cell growth factors in ECM prevents their systemic action on the vascular endothelium, thus maintaining a very low rate of endothelial cells turnover and vessel growth. On the other hand. release of bFGF from storage in ECM as a complex with HS fragment, may elicit localized endothelial cell proliferation and neovascularization in processes such as wound healing, inflammation and tumor development (24, 25).

Expression of heparanase by cells of the immune system: Heparanase activity correlates with the ability of activated cells of the immune system to leave the circulation and elicit both inflammatory and autoimmune responses. Interaction of platelets, granulocytes, T and B lymphocytes, macrophages and mast cells with the subendothelial ECM is associated with degradation of HS by a specific heparanase activity (6). The enzyme is released from intracellular compartments (e.g., lysosomes, specific granules. etc.) in response to various activation signals (e.g., thrombin, calcium ionophore, immune complexes. antigens. mitogens. etc.). suggesting its regulated involvement in inflammation and cellular immunity.

Some of the observations regarding the Heparanase enzyme were reviewed in reference No. 6 and are listed hereinibelow.

First, a proteolytic activity (plasminogen activator) and heparanase participate synergistically in sequential degradation of the ECM HSPG by inflammatory leukocytes and malignant cells.

Second, a large proportion of the platelet heparanase exists in a latent form, probably as a complex with chondroitin sulfate. The latent enzyme is activated by tumor cell-derived factor(s) and may then facilitate cell invasion through the vascular endothelium in the process of tumor metastasis.

Third, release of the platelet heparanase from α-granules is induced by a strong stimulant (i.e., thrombin), but not in response to platelet activation on ECM.

Fourth, the neutrophil heparaniase is preferentially and readily released in response to a threshold activation and upon incubation of the cells on ECM.

Fifth, contact of neutrophils with ECM inhibited release of noxious enzymes (proteases, lysozyme) and oxygen radicals, but not of enzymes (heparanase, gelatinase) which may enable diapedesis. This protective role of the subendothelial ECM was observed when the cells were stimulated with soluble factors but not with phagocytosable stimulants.

Sixth, intracellular heparaniase is secreted within minutes after exposure of T cell lines to specific antigens.

Seventh, mitogens (Con A, I,PS) induce synthesis and secretion of heparanase by normal T and B lymphocytes maintained in vitro. T lymphocyte heparanase is also induced by immunization with antigen in vivo.

Eighth, heparanase activity is expressed by pre-B lymphomas and B-lymphomas, but not by plasmacytomas and resting normal B lymphocytes.

Ninth, heparanase activity is expressed by activated macrophages during incubation with ECM, but there was little or no release of the enzyme into the incubation medium. Similar results were obtained with human myeloid leukemia cells induced to differentiate to mature macrophages.

Tenth, T-cell mediated delayed type hypersensitivity and experimental autoimmunity are suppressed by low doses of heparanase inhibiting non-anticoagulant species of heparin (30).

Eleventh, heparanase activity expressed by platelets, neutrophils and metastatic tumor cells releases active bFGF from SCM and basement membranes. Release of bFGF from storage in ECM may elicit a localized neovascular response in processes such as wound healing, inflammation and tumor development.

Twelfth, among the breakdown products of the ECM generated by heparanase is a tri-sulfated disaccharide that can inhibit T-cell mediated inflammation in vivo (31). This inhibition was associated with an inhibitory effect of the disaccharide on the production of biologically active TNFα- by activated T cells inl vitro (31).

Other potential therapeutic applications: Apart from its involvement in tumor cell metastasis, inflammation and autoimmunity, mammalian heparanase may be applied to modulate: bioavailability of heparin-binding growth factors (5); cellular responses to heparin-binding growth factors (e.g., bFGF, VEGF) and cytokines (IL-8) (31a, 29); cell interaction with plasma lipoproteins (32); cellular susceptibility to certain viral and some bacterial and protozoa infections (33, 33a, 33b); and disintegration of amyloid plaques (34). Heparanase may thus prove useful for conditions such as wound healing, angiogenesis, restenosis, atherosclerosis, inflammation, neurodegenerative diseases and viral infections. Mammalian heparanase can be used to neutralize plasma heparin. as a potential replacement of protamine. Anti-heparanase antibodies may be applied for immunodetection and diagnosis of micrometastases, autoimmune lesions and renal failure in biopsy specimens, plasma samples, and body fluids. Common use in basic research is expected.

The identification of the hpa gene encoding for heparanase enzyme will enable the production of a recombinant enzyme in heterologous expression systems. Availability of the recombinant protein will pave the way for solving the protein structure function relationship and will provide a tool for developing new inhibitors.

Viral infection: The presence of heparan sulfate on cell surfaces have been shown to be the principal requirement for the binding of Herpes Simplex (33) and Dengue (33a) viruses to cells and for subsequent infection of the cells. Removal of the cell surface heparan sulfate by heparanase may therefore abolish virus infection. In fact, treatment of cells with bacterial heparitinase (degrading heparan sulfate) or heparinase (degrading heparan) reduced the binding of two related animal herpes viruses to cells and rendered the cells at least partially resistant to virus infection (33). There are some indications that the cell surface heparan sulfate is also involved in HIV infection (33b).

Neurodegenerative diseases: Heparan sulfate proteoglycans were identified in the prion protein amyloid plaques of Genstmann-Straussler Syndrome, Creutzfeldt-Jakob disease and Scrape (34). Heparanase may disintegrate these amyloid plaques which are also thought to play a role in the pathogenesis of Alzheimer's disease.

Restenosis and Atherosclerosis: Proliferation of arterial smooth muscle cells (SMCs) in response to endothelial injury and accumulation of cholesterol rich lipoproteins are basic events in the pathogenesis of atherosclerosis and restenosis (35). Apart from its involvement in SMC proliferation (i.e., low affinity receptors for heparin-binding growth factors), HS is also involved in lipoprotein binding, retention and uptake (36). It was demonstrated that HSPG and lipoprotein lipase participate in a novel catabolic pathway that may allow substantial cellular and interstitial accumulation of cholesterol rich lipoproteins (32). The latter pathway is expected to be highly atherogenic by promoting accumulation of apoB and apoE rich lipoproteins (i.e. LDL, VLDL, chylomicrons), independent of feed back inhibition by the cellular sterol content. Removal of SMC HS by heparanase is therefore expected to inhibit both SMC proliferation and lipid accumulation and thus may halt the progression of restenosis and atherosclerosis.

There is thus a widely recognized need for, and it would be highly advantageous to have a polynucleotide encoding a polypeptide having heparanase activity, vectors including same, transduced cells expressing heparanase and a recombinant protein having heparanase activity.

SUMMARY OF THE INVENTION

According to the present invention there is provided a polynucleotide, referred to hereinbelow as hpa, hpa cDNA or hpa gene. encoding a polypeptide having heparanase activity, vectors including same, transduced cells expressing heparanase and a recombinant protein having heparanase activity.

Cloning of the human spa gene which encodes heparanase, and expression of recombinant heparanase by transfected host cells is reported.

A purified preparation of heparanase isolated from human hepatoma cells was subjected to tryptic digestion and microsequencing. The YGPDVGQPR (SEQ ID NO:8) sequence revealed was used to screen EST databases for homology to the corresponding back translated DNA sequence. Two closely related EST sequences were identified and were thereafter found to be identical. Both clones contained an insert of 1020 bp which included an open reading frame of 973 bp followed by a 27 bp of 3' untranslated region and a Poly A tail. Translation start site was not identified.

Cloning of the missing 5' end of hpa was performed by PCR amplification of DNA from placenta Marathon RACE cDNA composite using primers selected according to the EST clones sequence and the linkers of the composite. A 900 bp PCR fragment, partially overlapping with the identified 3' encodinig EST clones was obtained. The joined cDNA fragment (hpa), 1721 bp long (SEQ ID NO:9), contained an open reading frame which encodes a polypeptide of 543 amino acids (SEQ ID NO:10) with a calculated molecular weight of 61,192 daltons.

The ability of the hpa gene product to catalyze degradation of heparan sulfate in an in vitro assay was examined by expressing the entire open reading frame of hpa in insect cells, using the Baculovirus expression system. Extracts and conditioned media of cells infected with virus containing the hpa gene, demonstrated a high level of heparan sulfate degradation activity both towards soluble ECM-derived HSPG and intact ECM. This degradation activity was inhibited by heparin. Cells infected with a similar construct containing no hpa gene had no such activity nor did noninfected cells.

The expression pattern of hpa RNA in various tissues and cell lines was investigated using RT-PCR. It was found to be expressed only in tissues and cells previously known to have heparanase activity.

According to further features in preferred embodiments of the invention described below, provided is a polynucleotide fragment which includes a polynucleotide sequence encoding a polypeptide having heparanase catalytic activity.

According to still further features in the described preferred embodiments the polynucleotide fragment includes nucleotides 63–1691 of SEQ ID NO:9, which encode the entire human heparanase enzyme.

According to still further features in the described preferred embodiments provided is a polynucleotide fragment which includes a polynucleotide sequence capable of hybridizing with hpa cDNA, especially with nucleotides 1–721 of SEQ ID NO:9.

According to still further features in the described preferred embodiments the polynucleotide sequence which encodes the polypeptide having heparanase activity shares at least 60% homology, preferably at least 70% homology more preferably at least 80% homology, most preferably at least 90% homology with SEQ ID NO:9.

According to still further features in the described preferred embodiments the polynucleotide fragment according to the present invention includes a portion (fragment) of SEQ ID NO:9. For example, such fragments could include nucleotides 63–721 of SEQ ID NO:9 and/or a segment of SEQ ID NO:9 which encodes a polypeptide having the heparanase catalytic activity.

According to still further features in the described preferred embodiments the polypeptide encoded by the polynucleotide fragment includes an amino acid sequence as set forth in SEQ ID NO:10 or a functional part thereof.

According to still further features in the described preferred embodiments the polynucleotide sequence encodes a polypeptide having heparanase activity, which shares at least 60% homology, preferably at least 70% homology, more preferably at least 80% homology, most preferably at least 90% homology with SFQ ID NO: 10.

According to still further features in the described preferred embodiments the polynucleotide fragment encodes a polypeptide having heparanase activity, which may therefore be allelic, species and/or induced variant of the amino acid sequence set forth in SEQ ID NO:10. It is understood that any such variant may also be considered a homolog.

According to still further features in the described preferred embodiments provided is a single stranded polynucleotide fragment which includes a polynucleotide sequence complementary to at least a portion of a polynucleotide strand encoding a polypeptide having heparanase catalytic activity as described above.

According to still further features in the described preferred embodiments provided is a vector including a polynucleotide sequence encoding a polypeptide having heparanase catalytic activity.

The vector may be of any suitable type including but not limited to a phage, virus, plasmid, phagemid, cosmid, bacmid or even an artificial chromosome. The polynucleotide sequence encoding a polypeptide having heparanase catalytic activity may include any of the above described polynucleotide fragments.

According to still further features in the described preferred embodiments provided is a host cell Which includes an exogenous polynucleotide fragment including a polynucleotide sequence encoding a polypeptide having heparanase catalytic activity.

The exogenous polynucleotide fragment may be any of the above described fragments. The host cell may be of any type such as prokaryotic cell, eukaryotic cell, a cell line, or a cell as a portion of a multicellular organism (e.g., cells of a transgenic organism).

According to still further features in the described preferred embodiments provided is a recombinant protein including a polypeptide having heparanase catalytic activity.

According to still further features in the described preferred embodiments provided is a pharmaceutical composition comprising as an active ingredient a recombinant protein having heparanase catalytic activity.

According to still further features in the described preferred embodiments provided is a medical equipment comprising a medical device containing, as an active ingredient a recombinant protein having heparanase catalytic activity.

According to still further features in the described preferred embodiments provided is a heparanase overexpression system comprising a cell overexpressing heparanase catalytic activity.

The present invention can be used to develop new drugs to inhibit tumor cell metastasis, inflammation and autoimmunity. The identification of the hpa gene encoding for heparanase enzyme enables the production of a recombinant enzyme in heterologous expression systems.

BRIEF DESCRIPTION OF THE DRAWINGS

The invention herein described, by way of example only, with reference to the accompanying drawings, wherein:

FIG. 1 presents nucleotide sequence and deduced amino acid sequence of hpa cDNA. A single nucleotide difference at position 799 (A to T) between the EST (Expressed Sequence Tag) and the PCR amplified cDNA (reverse transcribed RNA) and the resulting amino acid substitution (Tyr to Phe) are indicated above and below the substituted unit, respectively. Cysteine residues and the poly adenylation consensus sequence are underlined. The asterisk denotes the stop codon TGA.

FIGS. 7a–b demonstrate degradation of sulfate labeled intact ECM by virus infected cells. High Five (7a) and Sf21 (7b) cells were plated on sulfate labeled ECM and infected (48 h. 28° C.) with pFhpa4 (●) or control pF1 (□) viruses. Control non-infected Sf21 cells (□) were plate on labeled ECM as well. The pH of the cultured medium was adjusted to 6.0–6.2, followed by 48 h incubation at 28° C. Sulfate labeled degradation fragments released into the incubation medium as analyzed by gel filtration on Sepharose 6B. HS degradation fragments were produced only by cells infected with the hpa containing virus.

FIG. 13 presents a comparison between nucleotide sequences of the human hpa and a mouse EST cDNA fragment (SEQ ID NO:12) which is 80% homologous to the 3' end (starting at nucleotide 1066 of SEQ ID NO:9) of the human hpa. The aligned termination codons are underlined.

DESCRIPTION OF THE PREFERRED EMBODIMENTS

Figure 2:
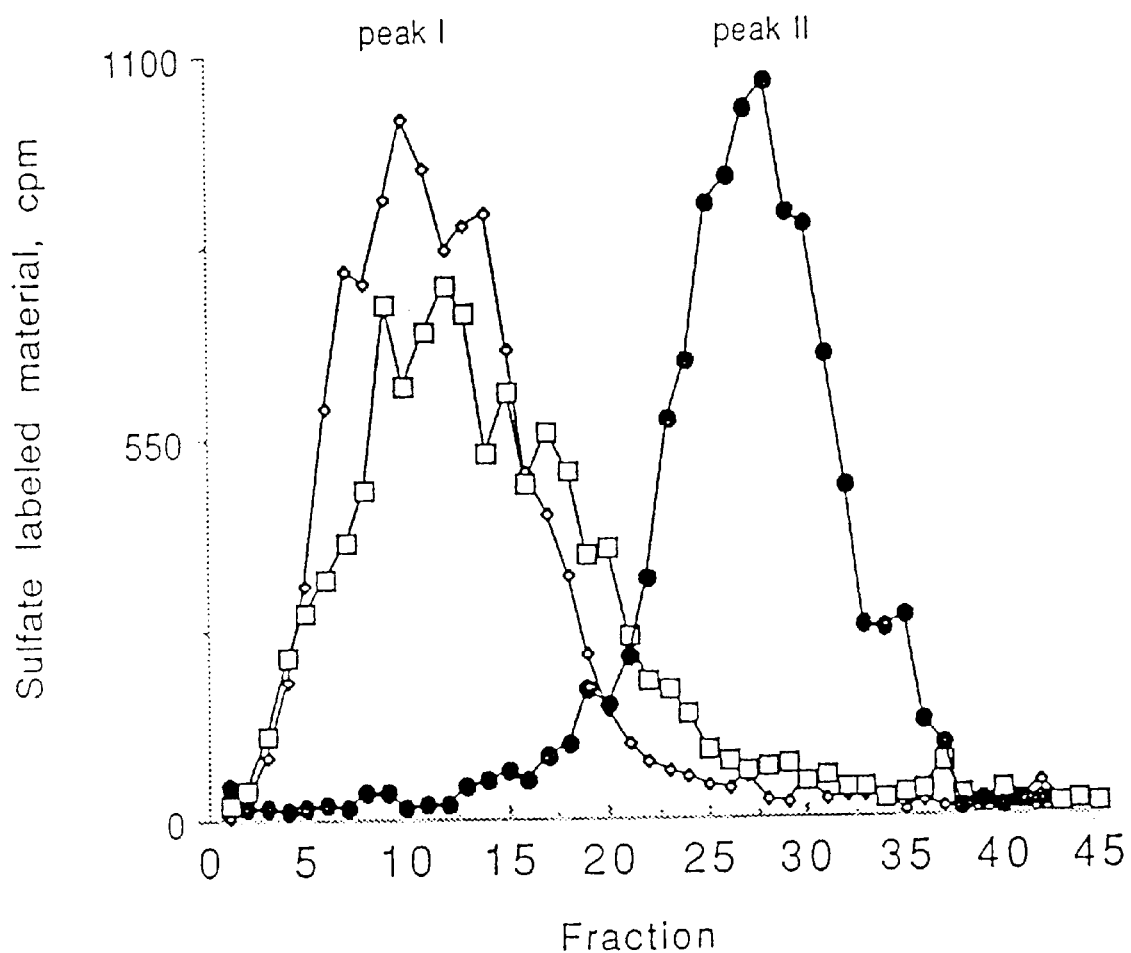
FIG. 2 demonstrates degradation of soluble sulfate labeled HSPG substrate by lysates of high Five cells infected with pFhpa2 virus. Lysates of High Five cells that were infected with pFhpa2 virus (●) or control pF2 virus (□) were incubated (18 h, 37° C.) with sulfate labeled ECM-derived soluble HSPG (peak I). The incubation medium was then subjected to gel filtration on Sepharose 6B. Low molecular weight HS degradation fragments (peak II) were produced only during incubation with the pF/hpa2 infected cells, but there was no degradation of the HSPG substrate (☆) by lysates of pF2 infected cells.

The present invention is of a polynucleotide, referred to hereinbelow interchangeably as hpa, hpa cDNA or hpa gene, encoding a polypeptide having heparanase activity, vectors including same, transduced cells expressing heparanase and a recombinant protein having heparanase activity.

The present invention can be used to develop treatments for various diseases, to develop diagnostic assays for these diseases and to provide new tools for basic research especially in the fields of medicine and biology.

Specifically, the present invention can be used to develop new drugs to inhibit tumor cell metastasis, inflammation and autoimmunity. The identification of the hpa gene encoding for the heparanase enzyme enables the production of a recombinant enzyme in heterologous expression systems.

Furthermore, the present invention can be used to modulate bioavailability of heparin-binding growth factors, cellular responses to heparin-binding growth factors (e.g., bFGF, VECGF) and cytokines (IL-8). cell interaction with plasma lipoproteins, cellular susceptibility to viral, protozoa and some bacterial infections, and disintegration of neurodegenerative plaques. Recombinant heparanase is thus potential treatment for wound healing, angiogenesis. restenosis, atherosclerosis, inflammation, neurodegenerative diseases (such as, for example, Genstmann-Straussler Syndrome, Crcutzfeldt-Jakob disease, Scrape and Alzheimier's disease) and certain viral and some bacterial and protozoa infections. Recombinant heparanase can be used to neutralize plasma heparin, as a potential replacement of protamine.

As used herein, the term "modulate" includes substantially inhibiting, slowing or reversing the progression of a disease. substantially ameliorating clinical symptoms of a disease or condition, or substantially preventing the appearance of clinical symptoms of a disease or condition. A "modulator" therefore includes an agent which may modulate a disease or condition. Modulation of viral, protozoa and bacterial infections includes any effect which substantially interrupts, prevents or reduces any viral, bacterial or protozoa activity and/or stage of the virus, bacterium or protozoan life cycle, or which reduces or prevents infection by the virus, bacterium or protozoan in a subject, such as a human or lower animal.

As used herein, the term "wound" includes any in jury to any portion of the body of a subject including. but not limited to, acute conditions such as thermal burns, chemical burns, radiation burns, burns caused by excess exposure to ultraviolet radiation such as sunburn, damage to bodily tissues such as the perineum as a result of labor and childbirth, including injuries sustained during medical procedures such as episiotomies, trauma-induced injuries including cuts, those injuries sustained in automobile and other mechanical accidents, and those caused by bullets, knives and other weapons, and post-surgical injuries, as well as chronic conditions such as pressure sores, bedsores, conditions related to diabetes and poor circulation, and all types of acne, etc.

Anti-heparanase antibodies, which may be raised against the recombinant enzyme, would be useful for immunodetection and diagnosis of micrometastases, autoimmune lesions and renal failure in biopsy specimens, plasma samples, and body fluids. Such antibodies may also serve as neutralizing agents for heparanase activity.

Cloning of the human hpa gene encoding heparanase and expressing recombinant heparanase by transfected cells is herein reported. This is the first mammalian heparanase gene to be cloned.

A purified preparation of heparanase isolated from human hepatoma cells was subjected to tryptic digestion and microsequencing.

The YGPDVGQPR (SEQ ID) NO:8) sequence revealed was used to screen EST databases for homology to the corresponding back translated DNA sequences.

Two closely related EST sequences were identified and were thereafter found to be identical.

Both clones contained an insert of 1020 bp which includes an open reading frame of 973 bp followed by a 3' untranslated region of 27 bp and a Poly A tail, whereas a translation start site was not identified.

Cloning of the missing 5' end was performed by PCR amplification of DNA from placenta Marathon RACE cDNA composite using primers selected according to the EST clones sequence and the linkers of the composite.

A 900 bp PCR fragment, partially overlapping with the identified 3' encoding EST clones was obtained. The joined cDNA fragment (hpa), 1721 bp long (SEQ ID NO:9), contained an open reading frame which encodes, as shown in FIG. 1 and SEQ ID NO:11, a polypeptide of 543 amino acids (SEQ ID NO:10) with a calculated molecular weight of 61,192 daltons.

A single nucleotide difference at position 799 (A to T) between the EST clones and the PCR amplified cDNA was observed. This difference results in a single amino acid substitution (Tyr to Phe) (FIG. 1). Furthermore, the published EST sequences contained an unidentified nucleotide, which following DNA sequencing of both the EST clones was resolved into two nucleotides G and C at positions 1630 and 1631 in SEQ ID NO:9, respectively).

The ability of the hpa gene product to catalyze degradation of heparan sulfate in an in vitro assay was examined by expressing the entire open reading frame in insect cells, using the 13Baculovirus expression system.

Extracts and conditioned media of cells infected with virus containing the hpa gene, demonstrated a high level of heparan sulfate degradation activity both towards soluble ECM-derived HSPG and intact ECM, which was inhibited by heparin, while cells infected with a similar construct containing no hpa gene had no such activity, nor did non-infected cells.

The expression pattern of hpa RNA in various tissues and cell lines was investigated using RT-PCR. It was found to be expressed only in tissues and cells previously known to have heparanase activity.

Thus, according to the present invention provided is a polynucleotide fragment (either DNA or RNA, either single stranded or double stranded) which includes a polynucleotide sequence encoding a polypeptide having heparanase catalytic activity.

The term "heparanase catalytic activity" or its equivalent term "heparanase activity" both refer to a mammalian endoglycosidase hydrolyzing activity which is specific for heparan or heparan sulfate proteoglycan substrates as opposed to the activity of bacterial enzymes (hepariniase I, II and III) which degrade heparin or heparan sulfate by means of β-elimination (37).

In a prefered embodiment of the invention the polynucleotide fragment includes nucleotides 63–1691 of SEQ ID NO:9, which encode the entire human heparaniase enzyme.

However, the scope of the present invention is not limited to human heparanase since this is the first disclosure of an open reading frame (ORF) encoding any mammalian heparanase. Using the hpa cDNA, parts thereof or synthetic oligonucleotides designed according to its sequence will enable one ordinarily skilled in the art to identify genomic and/or cDNA clones including homologous sequences from other mammalian species.

The present invention is therefore further directed at a polynucleotide fragment which includes a polynucleotide sequence capable of hybridizing (base pairing under either stringent or permissive hybridization conditions, as for example described in Sambrook, J., Fritsch, E. F., Maniatis, T. (1989) *Molecular Cloning. A Laboratory Manual*. Cold Spring Harbor laboratory Press, New York.) with hpa cDNA, especially with nucleotides 1–721 of SEQ ID NO:9.

In fact, any polynucleotide sequence which encodes a polypeptide having heparanase activity and which shares at least 60% homology, preferably at least 70% homology, more preferably at least 80% homology, most penetrably at least 90% homology with SEQ ID NO:9 is within the scope of the present invention.

The polynucleotide fragment according to the present invention may include any part of SEQ ID NO: 9. For example, it may include nucleotides 63–721 of SEQ ID NO:9, which is a novel sequence. However, it may include any segment of SEQ ID NO:9 which encodes a polypeptide having the heparanase catalytic activity.

When the phrase "encodes a polypeptide having heparanase catalytic activity" is used herein and in the claims section below it refers to the ability of directing the synthesis of a polypeptide which, if so required for its activity, following post translational modifications, such as but not limited to, proteolysis (e.g., removal of a signal peptide and of a pro- or preprotein sequence), methionine modification, glycosylation, alkylation (e.g., methylation), acetylation, etc., is catalyticaly active in degradation of. for example, ECM and cell surface associated HS.

In a petered embodiment of the invention the polypeptide encoded by the polynucleotide fragment includes an amino acid sequence as set forth in SEQ ID NO:10 or a functional part thereof, i.e., a portion harboring heparanase catalytic activity.

However, any polynucleotide fragment which encodes a polypeptide having heparanase activity is within the scope of the present invention. Therefore, the polypeptide may be allelic, species and/or induced variant of the amino acid sequence set forth in SEQ ID NO:10 or functional part thereof.

In fact, any polynucleotide sequence which encodes a polypeptide having heparanase activity, which shares at least 60% homology, preferably at least 70% homology, more preferably at least 80% homology, most preferably at least 90% homology with SEQ ID NO:10 is within the scope of the present invention.

The invention is also directed at providing a single stranded polynucleotide fragment which includes a polynucleotide sequence complementary to at least a portion of a polynucleotide strand encoding a polypeptide having heparanase catalytic activity as described above. The term "complementary" as used herein refers to the ability of base pairing.

The single stranded polynucleotide fragment may be DNA or RNA or even include nucleotide analogs (e.g., thioated nucleotides), it may be a synthetic oligonucleotide or manufactured by transduced host cells, it may be of any desired length which still provides specific base pairing (e.g., 8 or 10, preferably more, nucleotides long) and it may include mismatches that do not hamper base pairing.

The invention is further directed at providing a vector which includes a polynucleotide sequence encoding a polypeptide having heparanase catalytic activity.

The vector may be of any type. It may be a phage which infects bacteria or a virus which infects eukaryotic cells. It may also be a plasmid, phagemid, cosmid, bacmid or an artificial chromosome. The polynucleotide sequence encoding a polypeptide having heparanase catalytic activity may include any of the above described polynucleotide fragments.

The invention is further directed at providing a host cell which includes an exogenous polynucleotide fragment encoding a polypeptide having heparanase catalytic activity.

The exogenous polynucleotide fragment may be any of the above described fragments. The host cell may be of any type. It may be a prokaryotic cell, an eukaryotic cell, a cell line, or a cell as a portion of an organism. The exogenous polynucleotide fragment may be permanently or transiently present in the cell. In other words, transduced cells obtained following stable or transient transfection, transformation or transduction are all within the scope of the present invention.

The term "exogenous" as used herein refers to the fact that the polynucleotide fragment is externally introduced into the cell. Therein it may be present in a single of any number of copies, it may be integrated into one or more chromosomes at any location or be present as an extrachromosomal material.

The invention is further directed at providing a heparanase overexpression system which includes a cell overexpressing heparanase catalytic activity. The cell may be a host cell transiently or stably transfected or transformed with any suitable vector which includes a polynucleotide sequence encoding a polypeptide having heparanase activity and a suitable promoter and enhancer sequences to direct overexpression of heparanase. However, the overexpressing cell may also be a product of an insertion (e.g., via homologous recombination) of a promoter and/or enhancer sequence downstream to the endogenous heparanase gene of the expressing cell, which will direct overexpression from the endogenous gene. The term "overexpression" as used herein in the specification and claims below refers to a level of expression which is higher than a basal level of expression typically characterizing a given cell under otherwise identical conditions.

The invention is further directed at providing a recombinant protein including a polypeptide having heparanase catalytic activity.

The recombinant protein may be purified by any conventional protein purification procedure close to homogeneity and/or be mixed with additives. The recombinant protein may be manufactured using any of the cells described above. The recombinant protein may be in any form. It may be in a crystallized form, a dehydrated powder form or in solution. The recombinant protein may be useful in obtaining pure heparanase, which in turn may be useful in eliciting anti-heparanase antibodies, either poly or monoclonal antibodies. and as a screening active ingredient in an anti-heparanase inhibitors or drugs screening assay or system.

The invention is further directed at providing a pharmaceutical composition which include as an active ingredient a recombinant protein having heparanase catalytic activity.

Formulations for topical administration may include, but are not limited to, lotions, ointments, gels, creams, suppositories, drops, liquids, sprays and powders. Conventional pharmaceutical carriers, aqueous, powder or oily bases, thickeners and the like may be necessary or desirable. Coated condoms, stents, active pads, and other medical devices may also be useful. In fact the scope of the present invention includes any medical equipment such as a medical device containing, as an active ingredient, a recombinant protein having heparanase catalytic activity.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include, but are not limited to, sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons ordinarily skilled in the art can easily determine optimum dosages, dosing methodologies and repetition rates.

Reference is now made to the following examples, which together with the above descriptions, illustrate the invention in a non-limiting fashion.

EXAMPLES

The following protocols and experimental details are referenced in the Examples that follow:

Purification and characterization of heparanase from a human hepatoma cell line and human placenta: A human hepatoma cell line (Sk-Hep-1) was chosen as a source for purification of a human tumor-derived heparanase. Purification was essentially as described in U.S. Pat. No. 5,362.641 to Fuks, which is incorporated by reference as it fully set forth herein. Briefly, 500 liter, $5 \times 10^{11}$ cells were grown in suspension and the heparanase enzyme was purified about 240,000 fold by applying the following steps: (i) cation exchange (CM-Sephadex) chromatography performed at pH6.0, 0.3–1.4M NaCl gradient; (ii) cation exchange (CM-Sephadex) chromatography performed at pH7.4 in the presence of 0.1% CHAPS. 0.3–1.1M NaCl gradient; (iii) heparin-Sepharose chromatography performed at pH7.4 in the presence of 0.1% CHAPS 0.35–1.1M NaCl gradient, (iv) ConA-Sepharose chromatography performed at pH6.0 in buffer containing 0.1% CHAPS and 1M NaCl, elution with 0.25M α-methyl mannoside; and (v) HPLC cation exchange (Mono-S) chromatography performed at pH7.4 in the presence of 0.1% CHAPS, 0.25–1M NaCl gradient.

Active fractions were pooled, precipitated with TCA and the precipitate subjected to SDS polyacrylamide gel electrophoresis and/or tryptic digestion and reverse phase HPLC. Tryptic peptides of the purified protein were separated by reverse phase HPLC (C8 column) and homogeneous peaks were subjected to amino acid sequence analysis.

The purified enzyme was applied to reverse phase HPLC and subjected to N-terminal amino acid sequencing using the amino acid sequencer (Applied Biosystems).

Cells: Cultures of bovine corneal endothelial cells (BCECs) were established from steer eyes as previously described (19, 38). Stock cultures were maintained in DMEM (1 g glucose/liter) supplemented with 10% newborn calf serum and 5% FCS. bFGF (1 ng/ml) was added every other day during the phase of active cell growth (13, 14).

Preparation of dishes coated with ECM: BCECs (second to fifth passage) were plated into 4-well plates at an initial density of $2 \times 10^5$ cells/ml, and cultured in sulfate-free Fisher medium plus 5% dextran T-40 for 12 days. $Na_2^{35}SO_4$ (25 μCi/ml) was added on day 1 and 5 after seeding and the cultures were incubated with the label without medium change. The subendothelial ECM was exposed by dissolving (5 min., room temperature) the cell layer with PBS containing 0.5% Triton X-100 and 20 mM $NH_4OH$, followed by four washes with PBS. The ECM remained intact, free of cellular debris and firmly attached to the entire area of the tissue culture dish (19, 22).

To prepare soluble sulfate labeled proteoglycans (peak I material), the ECM was digested with trypsin (25 µg/ml, 6 h, 37° C.), the digest was concentrated by reverse dialysis and the concentrated material was applied onto a Sepharose 6B gel filtration column. The resulting high molecular weight material (Kav<0.2., peak I) was collected. More than 80% of the labeled material was shown to be composed of heparan sulfate proteoglycans (11, 39).

Heparaniase activity: Cells ($1\times10^6$/35-mm dish), cell lysates or conditioned media were incubated on top of $^{35}$S-labeled ECM (18 h 37° C.) in the presence of 20 mM phosphate buffer (pH 6.2). Cell lysates and conditioned media were also incubated with sulfate labeled peak I material (10–20 µl). The incubation medium was collected, centrifuged (18,000×g, 4° C., 3 min.), and sulfate labeled material analyzed by gel filtration on a Sepharose CL-6B column (0.9×30 cm). Fractions (0.2 ml) were eluted with PBS at a flow rate of 5 ml/h and counted for radioactivity using Bio-fluor scintillation fluid. The excluded volume ($V_o$) was marked by blue dextran and the total included volume ($V_t$) by phenol red. The latter was shown to comigrate with free sulfate (7, 11, 23). Degradation fragments of HS side chains were eluted from Sepharose 6B at 0.5<Kav<0.8 (peak II) (7, 11, 23). A nearly intact HSPG released from ECM by trypsin—and, to a lower extent, during incubation with PBS alone—was eluted next to $V_o$ (Kav<0.2, peak I). Recoveries of labeled material applied on the columns ranged from 85 to 95% in different experiments (11). Each experiment was performed at least three times and the variation of elution positions (Kav values) did not exceed +/-15%.

Cloning of hpa cDNA: cDNA clones 257548 and 260138 were obtained from the I.M.A.G.E Consortium (2130 Memorial Parkway SW, Hunstville, Ala. 35801). The cDNAs were originally cloned in EcoRI and NotI cloning sites in the plasmid vector pT3T7D-Pac. Although these clones are reported to be somewhat different, DNA sequencing demonstrated that these clones are identical to one another. Marathon RACE (rapid amplification of cDNA ends) human placenta (poly-A) cDNA composite was a gift of Prof. Yossi Shiloh of Tel Aviv University. This composite is vector free, as it includes reverse transcribed cDNA fragments to which double, partially single stranded adapters are attached on both sides. The construction of the specific composite employed is described in reference 39a.

Amplification of hp3 PCR fragment was performed according to the protocol provided by Clontech laboratories. The template used for amplification was a sample taken from the above composite. The primers used for amplification were:

First step: 5'-primer: AP1: 5'-CCATCCTAATACGACTCACTATAGGG C-3', SEQ ID NO:1; 3'-primer: HPL229: 5'-GTAGTGATGCCATGTAACTGA ATC-3', SEQ ID NO:2.

Second step: nested 5'-primer: AP2: 5'-ACTCACTATAGGGCTCGAGC GC-3', SEQ ID NO:3; nested 3'-primer: HPL171: 5'-GCATCTTAGCCGTCT TTCTTCG-3', SEQ ID NO:4. The HPL229 and HPL 171 were selected according to the sequence of the EST clones. They include nucleotides 933–956 and 876–897 of SEQ ID NO:9, respectively.

PCR program was 94° C.—4 min., followed by 30 cycles of 94° C.—40 sec. 62 ° C.—1 min., 72° C.—2.5 min. Amplification was performed with Expand High Fidelity (Boehringer Mannheim). The resulting ca. 900 bp hp3 PCR product was digested with BfrI and PvuII. Clone 257548 (phpa1) was digested with EcoR1, followed by end filing and was then further digested with BfrI. Thereafter the PvuII— BfrI fragment of the hp3 PCR product was cloned into the blunt end—BfrI end of clone papa I which resulted in having the entire cDNA cloned in pT3T7-pac vector, designated phpa2.

DNA Sequencing: Sequence determinations were performed with vector specific and gene specific primers, using an automated DNA sequencer (Applied Biosystems, model 373A). Each nucleotide was read from at least two independent primers.

Computer analysis of sequences: Database searches for sequence similarities were performed using the Blast network service. Sequence analysis and alignment of DNA and protein sequences were done using the DNA sequence analysis software package developed by the Genetic Computer Group (GCG) at the University of Wisconsin.

RT-PCR: RNA was prepared using TRI-Reagent (Molecular research center Inc.) according to the manufacturer instructions. 1.25 µg were taken for reverse transcription reaction using MuML,V Reverse transcriptase (Gibco BRL) and Oligo $(dT)_{15}$ primer, SEQ ID NO:5, (Promega). Amplification of the resultant first strand cDNA was performed with Taq polymerase (Promega). The following primers were used:

HPU-355: 5'-TTCGATCCCAAGAAGGAATCAAC-3', SEQ ID NO:6, nucleotides 372–394 in SEQ ID NO:9 or 11.

HPL-229: 5'-GTAGTGATGCCATGTAACTGA-3', SEQ ID NO:7, nucleotides 933–956 in SEQ ID NO:9 or 11.

PCR program: 94° C.—4 min., followed by 30 cycles of 94° C.—40 sec., 62° C. 1 min. 72° C.—1 min.

Expression of recombinant heparanase in insect cells: Cells, High Five and Sf21 insect cell lines were maintained as monolayer cultures in SF900II-SFM medium (GibcoBPL,).

Recombinant Baculovirus: Recombinant virus containing the hpa gene was constructed using the Bac to Bac system (GibcoBRL). The transfer vector pFastBac was digested with SalI and NotI and ligated with a 1.7 kb fragment of phpa2 digested with XhoI and NotI. The resulting plasmid was designated pFasthpa2. An identical plasmid designated pFasthpa4 was prepared as a duplicate and both independently served for further experimentations. Recombinant bacmid was generated according to the instructions of the manufacturer with pFasthpa2, pFasthpa4 and with pFastBac. The latter served as a negative control. Recombinant bacmid DNAs were transfected into Sf21 insect cells. Five days after transfection recombinant viruses were harvested and used to infect High Five insect cells, $3\times10^6$ cells in T-25 flasks. Cells were harvested 2–3 days after infection. $4\times10^6$ cells were centrifuged and resuspended in a reaction buffer containing 20 mM phosphate citrate buffer, 50 mM NaCl. Cells underwent three cycles of freeze and thaw and lysates were stored at −80° C. Conditioned medium was stored at 4° C.

Figure 10A:
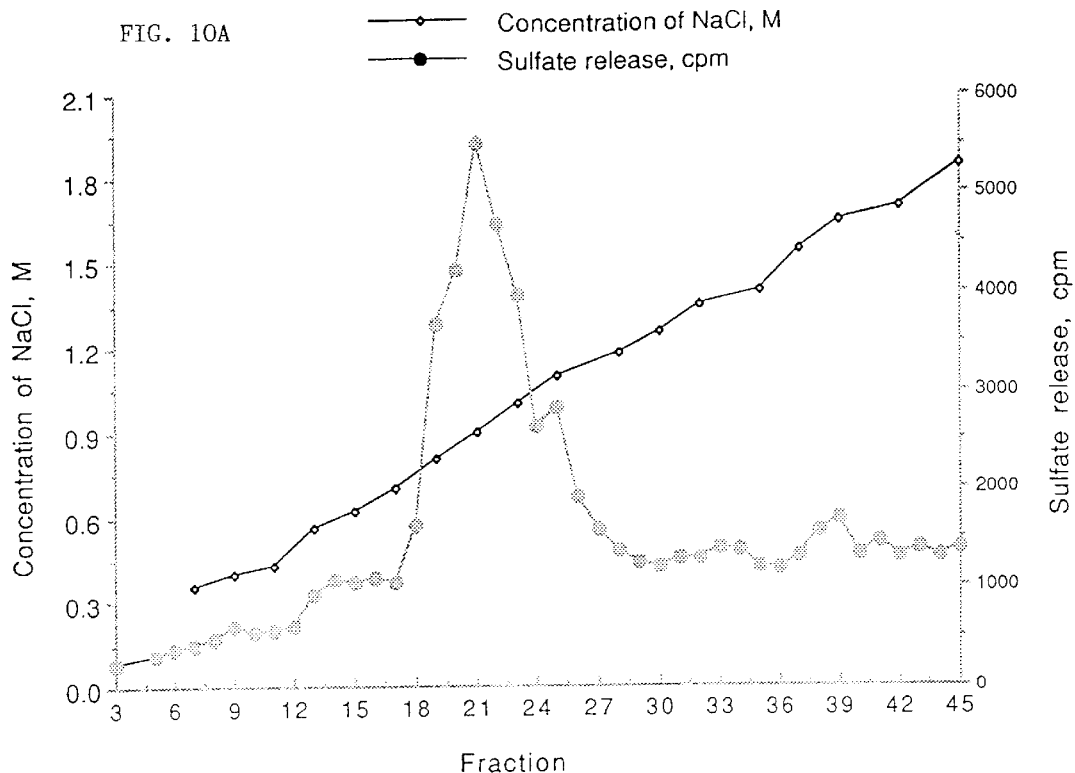
FIGS. 10a–b demonstrate purification of recombinant heparanase on heparin-Sepharose. Culture medium of Sf21 cells infected with pFhpa4 virus was subjected to heparin-Sepharose chromatography. Elution of fractions was performed with 0.35–2M NaCl gradient (☆). Heparanase activity in the eluted fractions is demonstrated in FIG. 10a (●). Fractions 15–28 were subjected to 15% SDS-polyacrylamide gel electrophoresis followed by silver nitrate staining. A correlation is demonstrated between a major protein band (MW~63,000) in fractions 19–24 and heparanase activity.

Partial purification of recombinant heparanase: Partial purification of recombinant heparanase was performed by heparin-Sepharose column chromatography followed by Superdex 75 column gel filtration. Culture medium (150 ml) of Sf21 cells infected with pFhpa4 virus was subjected to heparin-Sepharose chromatography. Elution of 1 ml fractions was performed with 0.35–2M NaCl gradient in presence of 0.1% CHAPS and 1 mM DTT in 10 mM sodium acetate buffer. pH5.0. A 25 μl sample of each fraction was tested for heparanase activity. Heparanase activity was eluted at the range of 0.65–1.1M NaCl (fractions 18–26 FIG. 1a). 5 μl of each fraction was subjected to 15% SDS-polyacrylamide gel electrophoresis followed by silver nitrate staining. Active fractions eluted from heparin-Sepharose (FIG. 10a) were pooled and concentrated (×6) on YM3 cut-off membrane. 0.5 ml of the concentrated material was applied onto 30 ml Superdex 75 FPLC column equilibrated with 10 mM sodium acetate buffer, pH 5.0, containing 0.8M NaCl, 1 mM DTT and 0.1% ChAPS. Fractions (0.56 ml) were collected at a flow rate of 0.75 ml/min. Aliquots of each fraction were tested for heparanase activity and were subjected to SDS-polyacrylamide gel electrophoresis followed by silver nitrate staining (FIG. 11b).

Example 1

Cloning of the hpa gene

Purified fraction of heparanase isolated from human hepatoma cells (SK-Hep-1) was subjected to tryptic digestion and microsequencing. EST (Expressed Sequence Tag) databases were screened for homology to the back translated DNA sequences corresponding to the obtained peptides. Two EST sequences (accession Nos. N41349 and N45367) contained a DNA sequence encoding the peptide YGPD-VGQPR (SEQ ID NO:8). These two sequences were derived from clones 257548 and 260138 (I.M.A.G.E Consortium) prepared from 8 to 9 weeks placenta cDNA library (Soares). Both clones which were found to be identical contained an insert of 1020 bp which included an open reading frame (ORF) of 973 bp followed by a 3' untranslated region of 27 bp and a Poly A tail. No translation start site (AUG) was identified at the 5' end of these clones.

Cloning of the missing 5' end was performed by PCR amplification of DNA from a placenta Marathon RACE cDNA composite. A 900 bp fragment (designated hp3), partially overlapping with the identified 3' encoding EST clones was obtained.

The joined eDNA fragment, 1721 bp long (SEQ ID NO:9), contained an open reading frame which encodes, as shown in FIG. 1 and SEQ ID NO:11, a polypeptide of 543 amino acids (SEQ ID NO:10) with a calculated molecular weight of 61,192 daltons. The 3' end of the partial cDNA inserts contained in clones 257548 and 260138 started at nucleotide $G^{721}$ of SEQ ID NO:9 and FIG. 1.

As further shown in FIG. 1, there was a single sequence discrepancy between the EST clones and the PCR amplified sequence, which led to an amino acid substitution from $Tyr^{246}$ in the EST to $Phe^{246}$ in the amplified cDNA. The nucleotide sequence of the PCR amplified cDNA fragment was verified from two independent amplification products. The new gene was designated hpa.

As stated above, the 3' end of the partial cDNA inserts contained in EST clones 257548 and 260138 started at nucleotide 721 of spa (SEQ ID NO:9). The ability of the hpa cDNA to form stable secondary structures, such as stem and loop structures involving nucleotide stretches in the vicinity of position 721 was investigated using computer modeling. It was found that stable stem and loop structures are likely to be formed involving nucleotides 698–724 (SEQ ID NO:9). In addition, a high GC content, up to 70%, characterizes the 5' end region of the hpa gene, as compared to about only 40% in the 3' region. These findings may explain the immature termination and therefore lack of 5' ends in the EST clones.

To examine the ability of the hpa gene product to catalyze degradation of heparan sulfate in an in vitro assay the entire open reading frame was expressed in insect cells, using the Baculovirus expression system. Extracts of cells, infected with virus containing the hpa gene, demonstrated a high level of heparan sulfate degradation activity, while cells infected with a similar construct containing no hpa gene had no such activity, nor did non-infected cells. These results are further demonstrated in the following Examples.

Example 2

Degradation of soluble ECM-derived HSPG

Monolayer cultures of High Five cells were infected (72 h, 28° C.) with recombinant Baculuvirus containing the pFasthpa plasmid or with control virus containing an insert free plasmid. The cells were harvested and lysed in heparanase reaction buffer by three cycles of freezing and thawing. The cell lysates were then incubated (18 h, 37° C.) with sulfate labeled, ECM-derived HSPG (peak I), followed by gel filtration analysis (Sepharose 6B) of the reaction mixture.

As shown in FIG. 2, the substrate alone included almost entirely high molecular weight (Mr) material eluted next to $V_o$ (peak I fractions 5–20, Kav<0.35). A similar elution pattern was obtained when the HSPG substrate was incubated with lysates of cells that were infected with control virus. In contrast, incubation of the HSPG substrate with lysates of cells infected with the hpa containing virus resulted in a complete conversion of the high Mr substrate into low Mr labeled degradation fragments (peak II, fractions 22–35, 0.5<Kav<0.75).

Fragments eluted in peak II were shown to be degradation products of heparan sulfate, as they were (i) 5- to 6-fold smaller than intact heparan sulfate side chains (Kav approx. 0.33) released from ECM by treatment with either alkaline borohydride or papain; and (ii) resistant to further digestion with papain or chondroitinase ABC, and susceptible to deamination by nitrous acid (6, 11).

Similar results (not shown) were obtained with Sf21 cells. Again, heparanase activity was detected in cells infected with the hpa containing virus (pFhpa), but not with control virus (pF). This result was obtained with two independently generated recombinant viruses. Lysates of control not infected High Five cells hailed to degrade the HSPG substrate.

In subsequent experiments, the labeled HSPG substrate was incubated with medium conditioned by infected High Five or Sf21 cells.

Figure 3A:
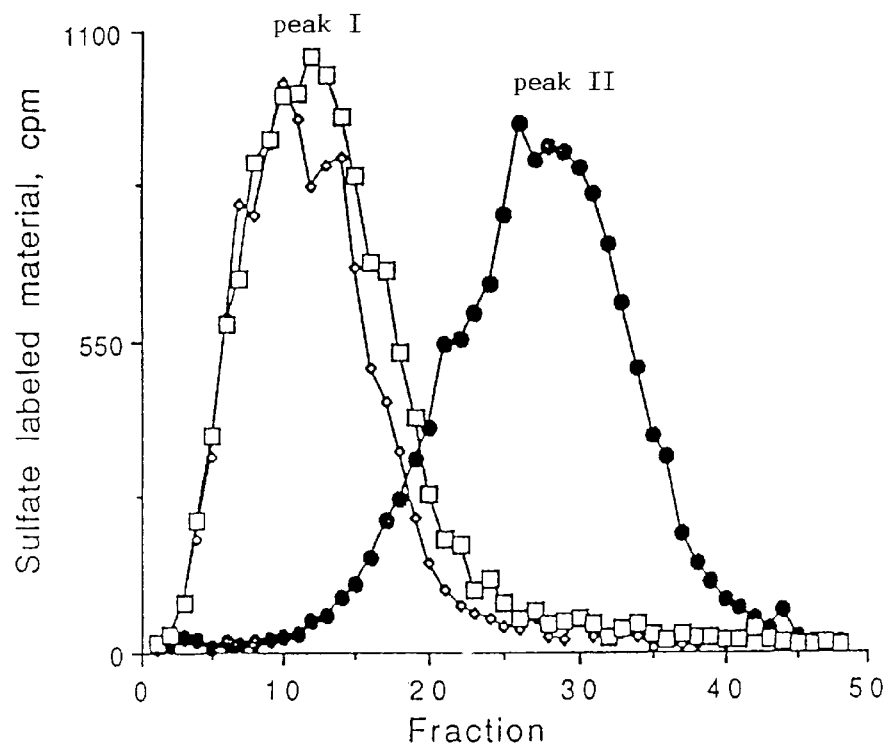
FIGS. 3a–b demonstrate degradation of soluble sulfate labeled HSPG substrate by the culture medium of pFhpa2 and pFhpa4 infected cells. Culture media of High Five cells infected with pFhpa2 (3a) or pFhpa4 (3b) viruses (●), or with control viruses (□) were incubated (18 h, 37° C.) with sulfate labeled ECM-derived soluble HSPG (peak I, ☆). The incubation media were then subjected to gel filtration on Sepharose 6B. Low molecular weight HS degradation fragments (peak II) were produced only during incubation with the hpa gene containing viruses. There was no degradation of the HSPG substrate by the culture medium of cells infected with control viruses.
Figure 3B:
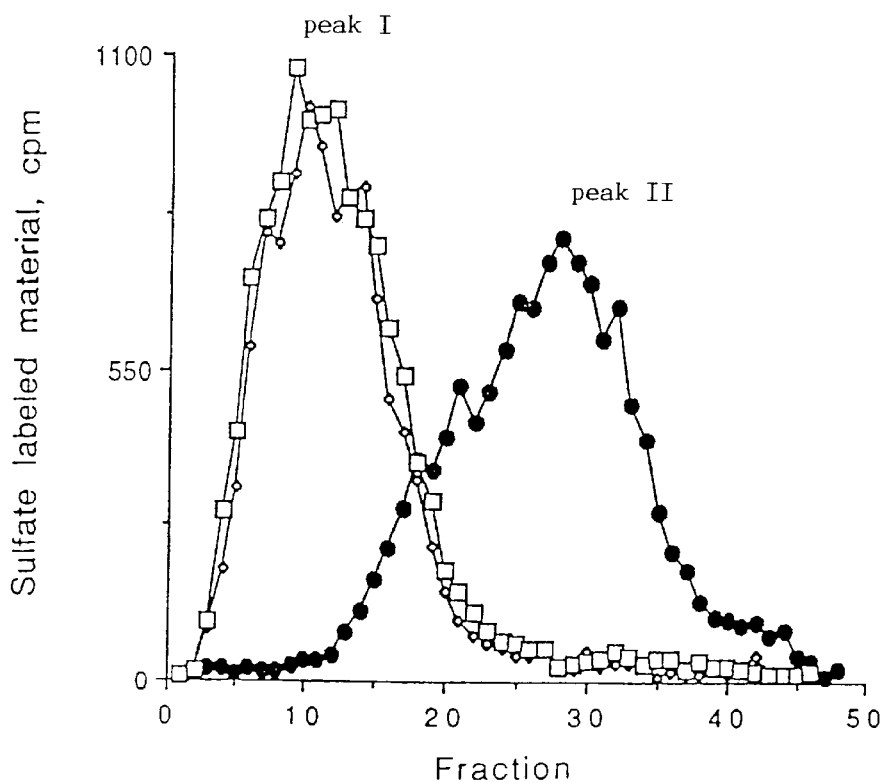

As shown in FIGS. 3a–b, heparanase activity, reflected by the conversion of the high Mr peak I substrate into the low Mr peak II which represents HS degradation fragments, was found in the culture medium of cells infected with the pFhpa2 or pFhpa4 viruses, but not with the control pF1 or pF2 viruses. No heparanase activity was detected in the culture medium of control non-infected High Five or Sf21 cells.

Figure 4:
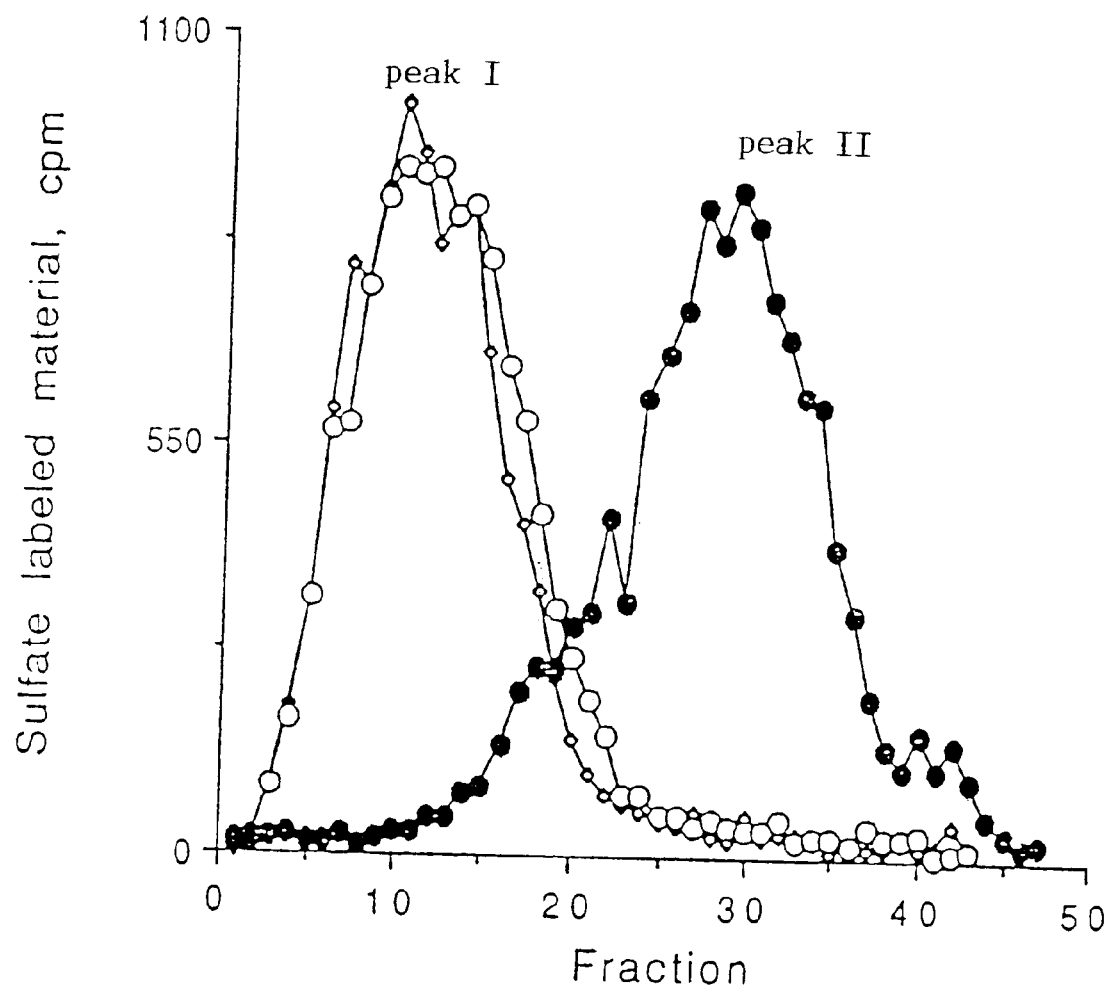
FIG. 4 presents size fractionation of heparanase activity expressed by pFhpa2 infected cells. Culture medium of pFhpa2 infected High Five cells was applied onto a 50 kDa cut-off membrane. Heparanase activity (conversion of the peak I substrate, (☆) into peak II HS degradation fragments) was found in the high (>50 kDa) (●), but not low (<50 kDa) (○) molecular weight compartment.

The medium of cells infected with the pFhpa4 virus was passed through a 50 kDa cut off membrane to obtain a crude estimation of the molecular weight of the recombinant heparanase enzyme. As demonstrated in FIG. 4, all the enzymatic activity was retained in the upper compartment and there was no activity in the flow through (<50 kDa) material. This result is consistent with the expected molecular weight of the hpa gene product.

In order to further characterize the Spa product the inhibitory effect of heparin, a potent inhibitor of heparanase mediated HS degradation (40) was examined.

Figure 5A:
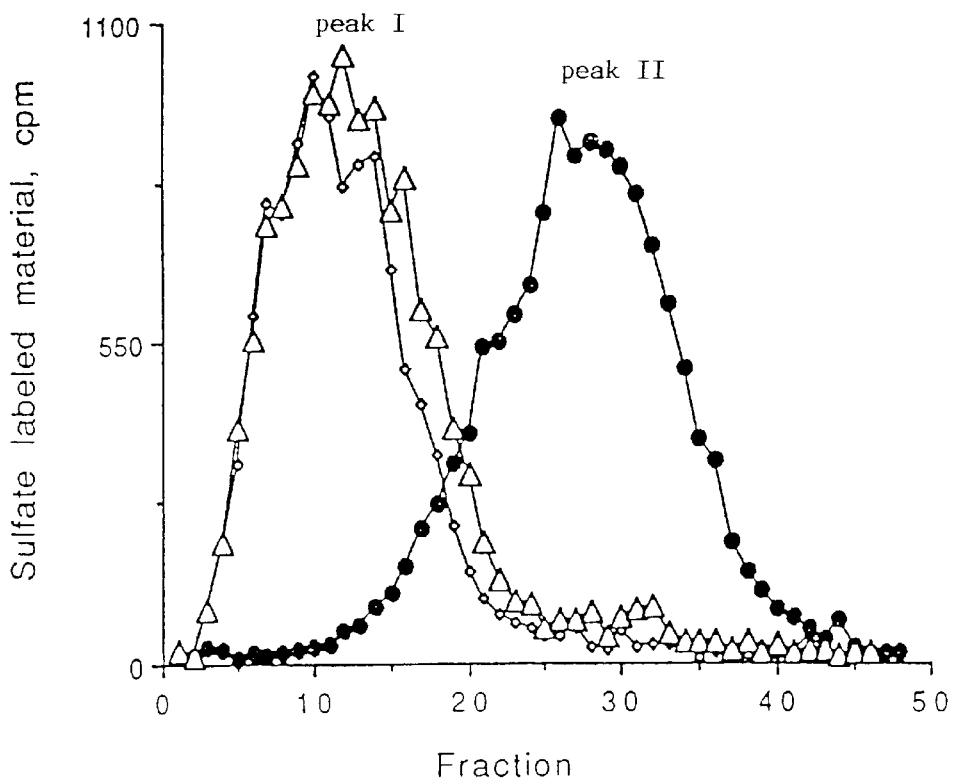
FIGS. 5a–b demonstrate the effect of heparin on heparanase activity expressed by pFhpa2 and pFhpa4 infected High Five cells. Culture media of pFhpa2 (5a) and pFhpa4 (5b) infected High Five cells were incubated (18 h, 37° C. with sulfate labeled ECM-derived soluble HSPG (peak I ☆) in the absence (●) or presence (Δ) of 10 μg/ml heparin. Production of low molecular weight HS degradation fragments was completely abolished in the presence of heparin, a potent inhibitor of heparanase activity (6. 7).
Figure 5B:
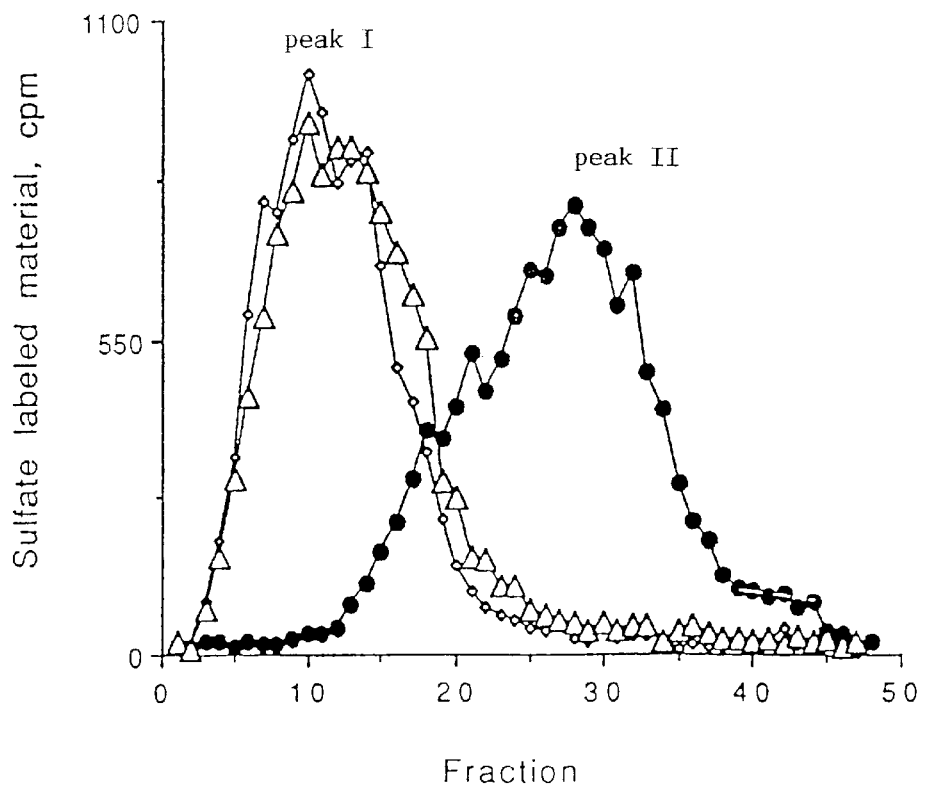
Figure 6A:
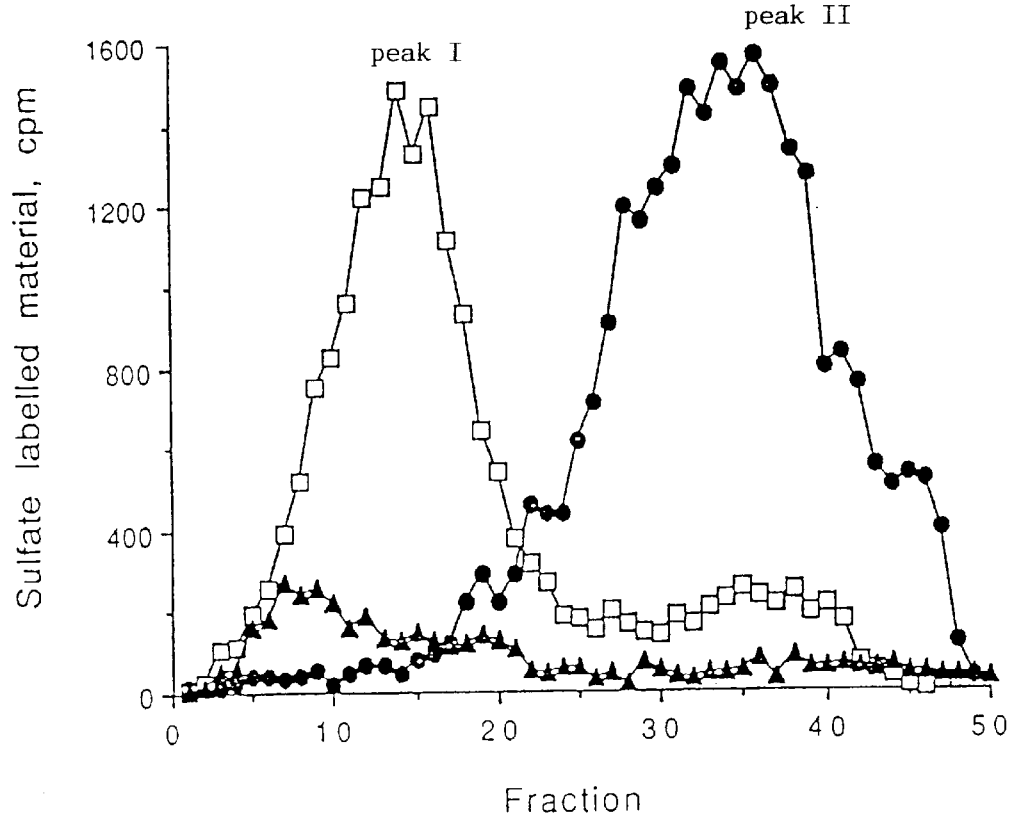
FIGS. 6a–b demonstrate degradation of sulfate labeled intact ECM by virus infected High Five and Sf21 cells. High Five (6a) and SF21 (6b) cells were plated on sulfate labeled ECM and infected (48 h, 28° C.) with pFhpa4 (●) or control pF1(□) viruses. Control non-infected Sf21 cells (□) were plated on the labeled ECM as well. The pH of the cultured medium was adjusted to 6.0–6.2 followed by 24 incubation at 37° C. Sulfate labeled material released into the incubation medium was analyzed by gel filtration on Sepharose 6B. HS degradation fragments were produced only by cells infected with the hpa containing virus.
Figure 6B:
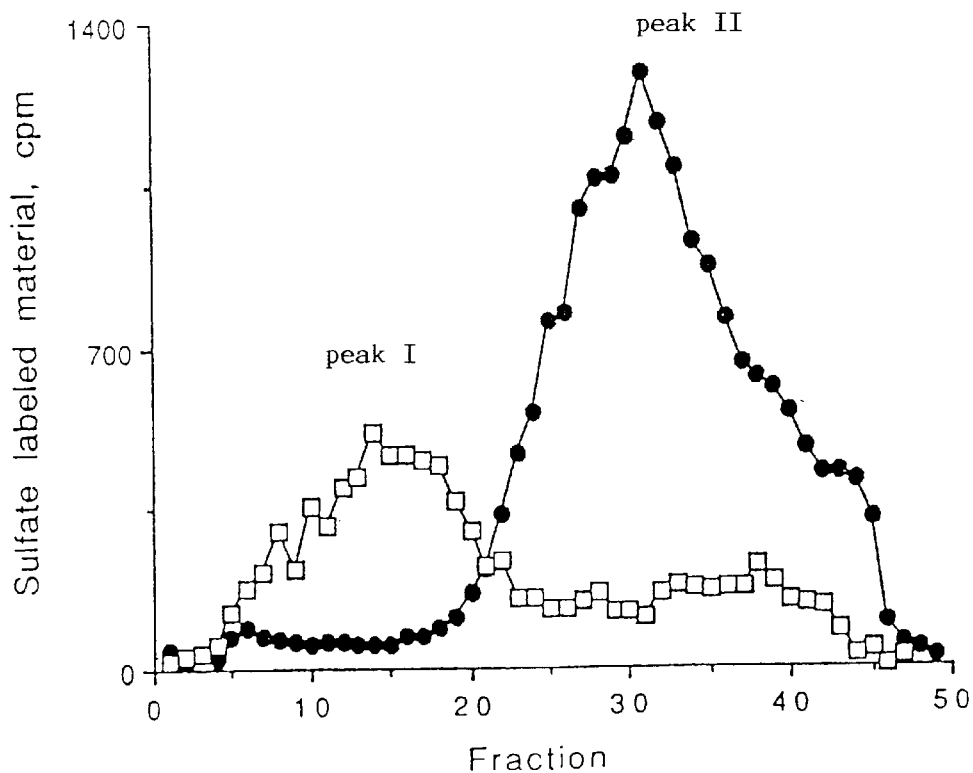

As demonstrated in FIGS. 5a–b, conversion of the peak I substrate into peak II HS degradation fragments was completely abolished in the presence of heparin.

Altogether, these results indicate that the heparanase enzyme is expressed in all active form by insect cells infected with Baculovirus containing the newly identified human hpa gene.

Example 3

Degradation of HSPG in intact ECM

Next, the ability of intact infected insect cells to degrade HS in intact naturally produced ECM was investigated. For this purpose, High Five or Sf21 cells were seeded on metabolically sulfate labeled ECM followed by infection (48 h. 28° C.) with either the pFhpa4 or control pF2 viruses. The pH of the medium was then adjusted to pH6.2–6.4 and the cells further incubated with the labeled ECM for another 48 h at 28° C. or 24 h at 37° C. Sulfate labeled material released into the incubation medium was analyzed by gel filtration on Sepharose 6B.

As shown in FIGS. 6a–b and 7a–b, incubation of the ECM with cells infected with the control pF2 virus resulted in a constant release of labeled material that consisted almost entirely (>90%) of high Mr fragments (peak I) eluted with or next to $V_o$. It was previously shown that a proteolytic activity residing in the ECM itself and/or expressed by cells is responsible for release of the high Mr material (6). This nearly intact HSPG provides a soluble substrate for subsequent degradation by heparanase. as also indicated by the relatively large amount of peak I material accumulating when the heparanase enzyme is inhibited by heparin (6, 7, 12, FIG. 9). On the other hand, incubation of the labeled ECM with cells infected with the pFhpa4 virus resulted in release of 60–70% of the ECM-associated radioactivity in the form of low Mr sulfate-labeled fragments (peak II, 0.5<Kav<0.75), regardless of whether the infected cells were incubated with the ECM at 28° C. or 37° C. Control intact non-infected Sf21 or High Five cells failed to degrade the ECM HS side chains.

Figure 8A:
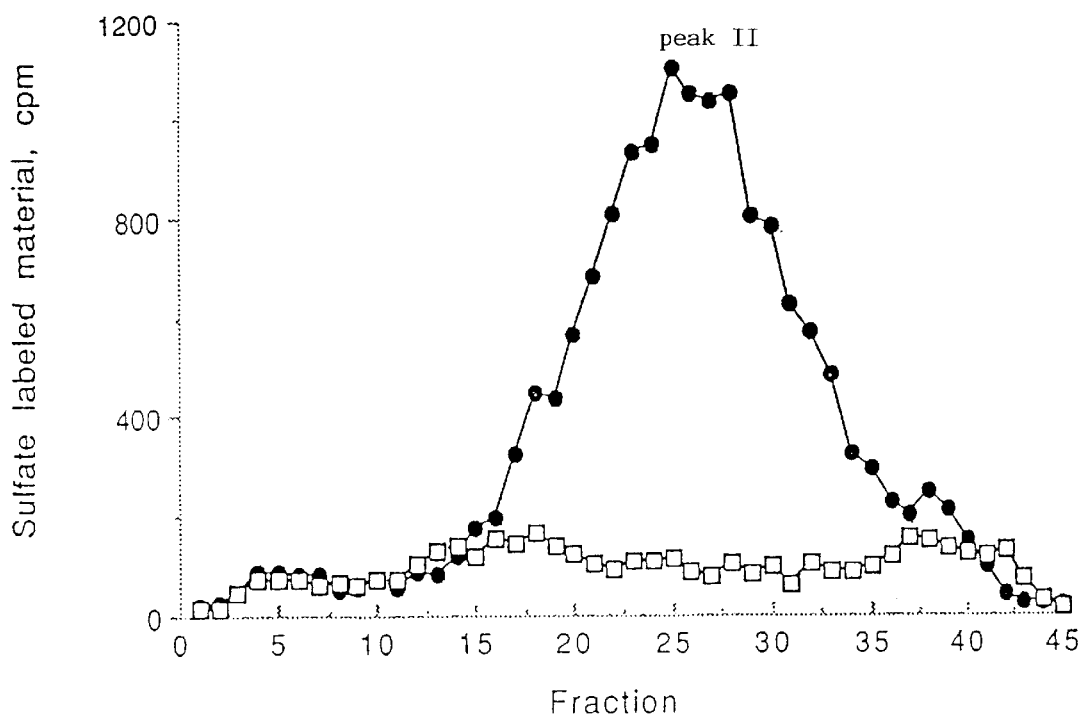
FIGS. 8a–b demonstrate degradation of sulfate labeled intact ECM by the culture medium of pFhpa4 infected cells. Culture media of High Five (8a) and Sf21 (8b) cells that were infected with pFhpa4 (●) or control pF1 (□) viruses were incubated (48 h, 37° C., pH6.0) with intact sulfate labeled ECM. The ECM was also incubated with the culture medium of control non-infected Sf21 cells (□). Sulfate labeled material released into the reaction mixture was subjected to gel filtration analysis. Heparanase activity was detected only in the culture medium of pFhpa4 infected cells.
Figure 8B:
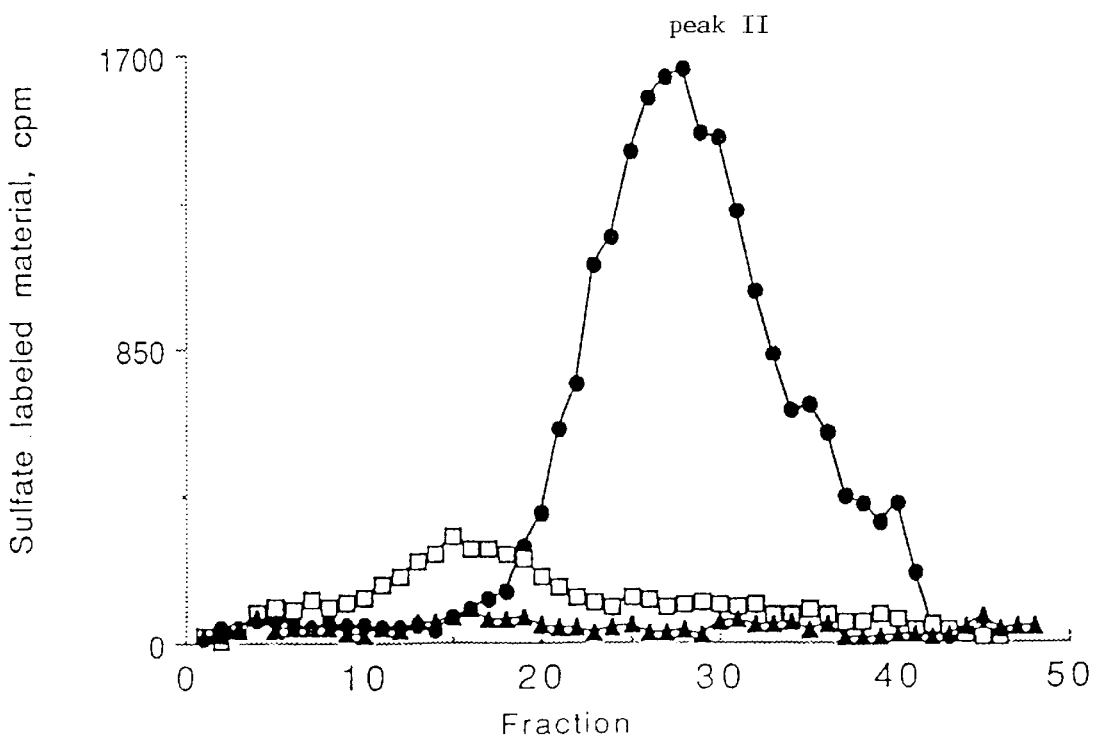
Figure 9A:
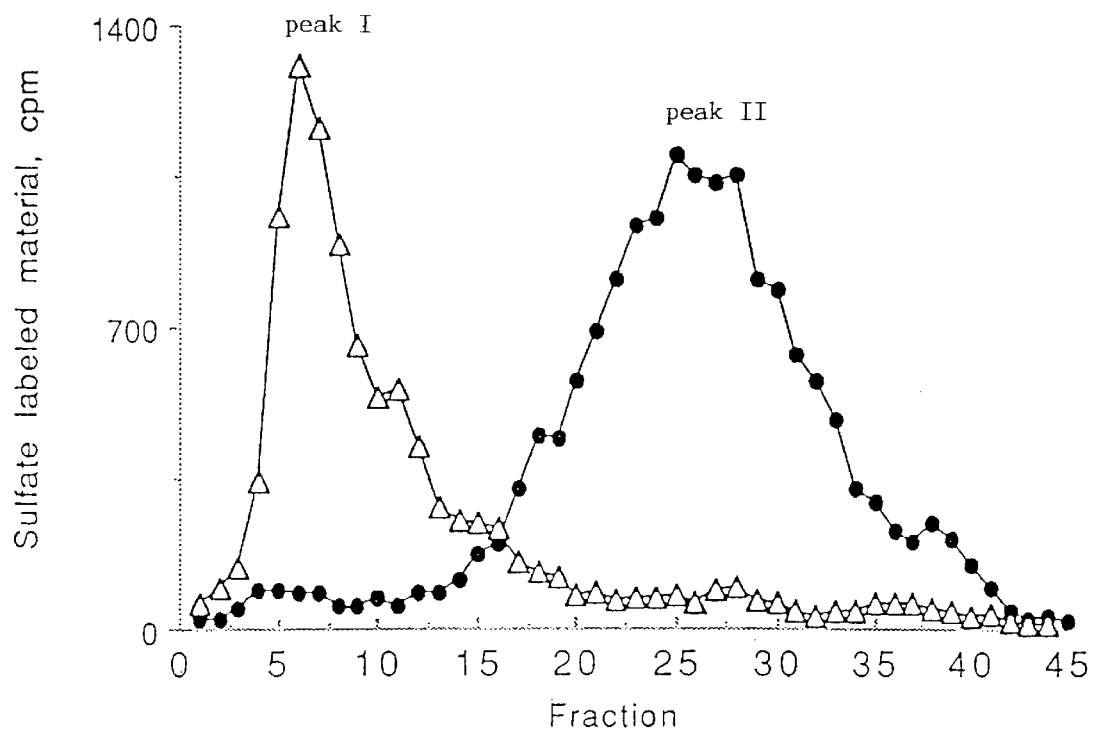
FIGS. 9a–b demonstrate the effect of heparin on heparanase activity in the culture medium of pFhpa4 infected cells. Sulfate labeled ECM was incubated (24 h, 37° C., pH 6.0) with culture medium of pFhpa4 infected High Five (9a) and Sf21 (9b) cells in the absence (●) or presence (Δ) of 10 μ/ml heparin. Sulfate labeled material released into the incubation medium was subjected to gel filtration on Sepharose 6B. Heparanase activity (production of peak II HS degradation fragments) was completely inhibited in the presence of heparin.
Figure 9B:
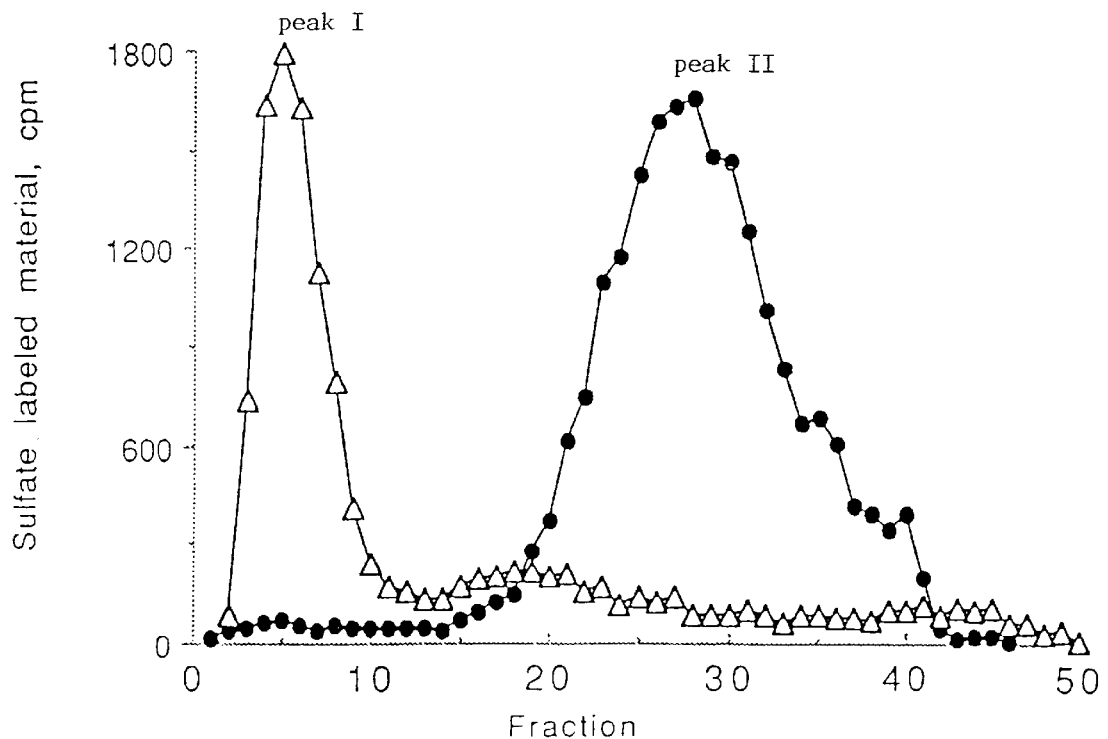

In subsequent experiments, as demonstrated in FIGS. 8a–b, High Five and Sf21 cells were infected (96 h, 28° C.) with pFhpa4 or control pF1 viruses and the culture medium incubated with sulfate-labeled ECM. Low Mr HS degradation fragments were released from the ECM only upon incubation with medium conditioned by pFhpa4 infected cells. As shown in FIG. 9, production of these fragments was abolished in the presence of heparin. No heparanase activity was detected in the culture medium of control, non-infected cells. These results indicate that the heparanase enzyme expressed by cells infected with the pFhpa4 virus is capable of degrading HS when complexed to other macromolecular constituents (i.e. fibronectin, laminin, collagen) of a naturally produced intact ECM, in a manner similar to that reported for highly metastatic tumor cells or activated cells of the immune system (6, 7).

Example 4

Purification of Recombinant Heparaniase

Figure 10B:
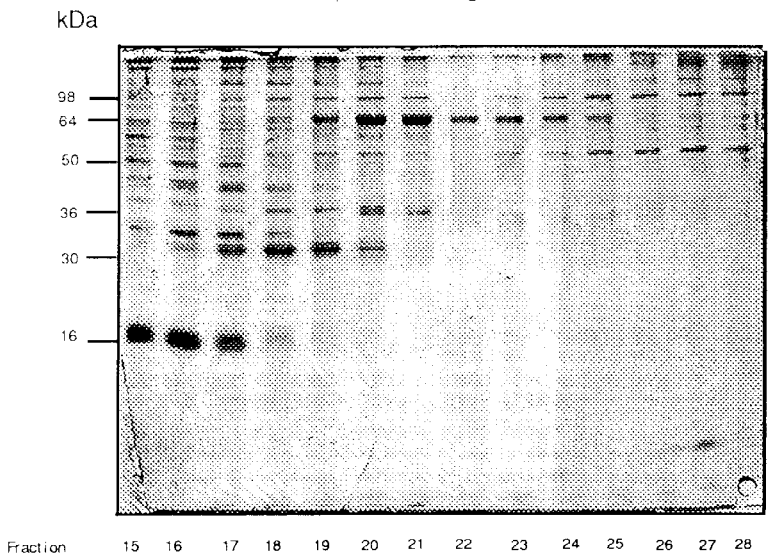
Figure 11A:
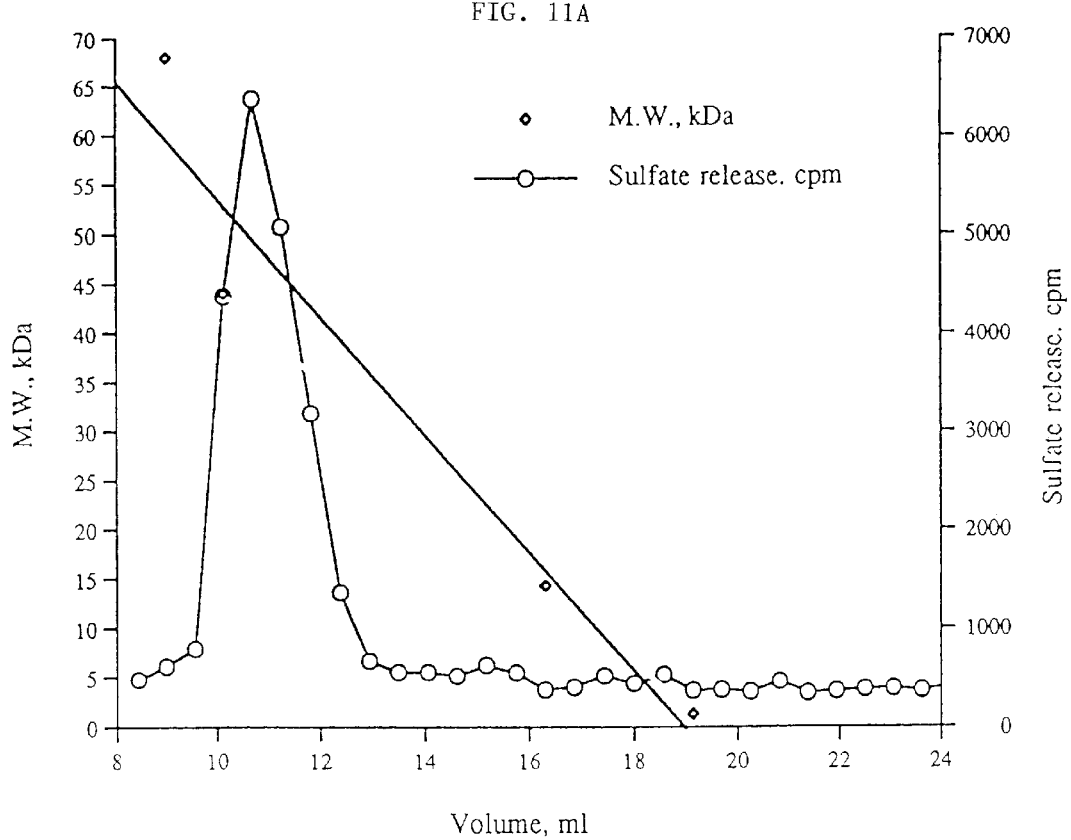
FIGS. 11a–b demonstrate purification of recombinant heparaniase on a Superdex 75 gel filtration column. Active fractions eluted from heparin-Sepharose (FIG. 10a) were pooled, concentrated and applied onto Superdex 75 FPLC column. Fractions were collected and aliquots of each fraction were tested for heparanase activity (○, FIG. 11a) and analyzed by SDS-polyacrylamide gel electrophoresis followed by silver nitrate staining (FIG. 11b). A correlation is seen between the appearance of a major protein band (MW~63,000) in fractions 4=7 and heparanase activity.
Figure 11B:
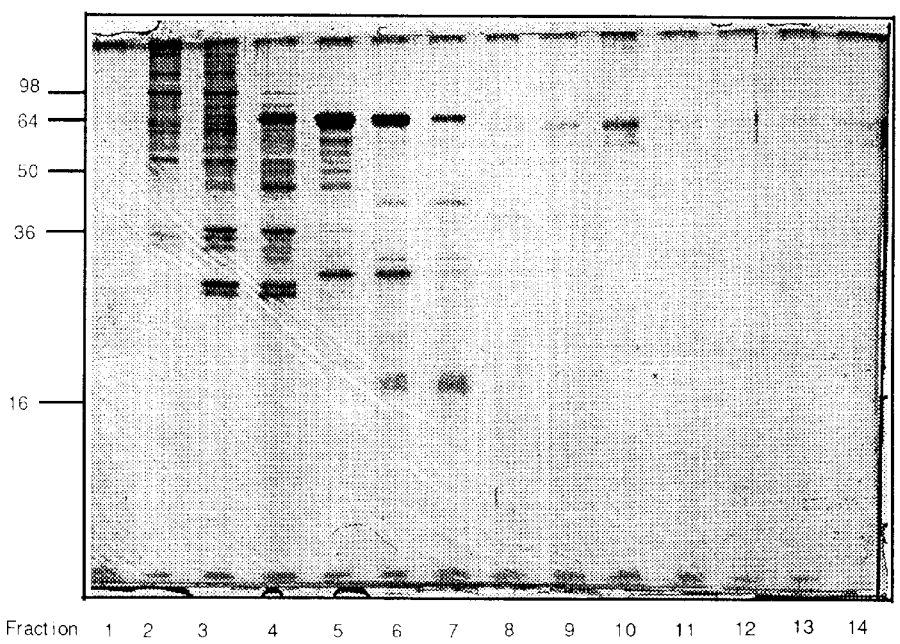

The recombinant heparaniase was partially purified from medium of pFhpa4 infected Sf21 cells by Heparin-Sepharose chromatography (FIG. 10a) followed by gel filtration of the pooled active fractions over an FPLC Superdex 75 column (FIG. 11a). A~63 kDa protein was observed, whose quantity, as was detected by silver stained SDS-polyacrylamide gel electrophoresis, correlated with heparanase activity in the relevant column fractions (FIGS. 10b and 11b, respectively). This protein was not detected in the culture medium of cells infected with the control pF1 virus and was subjected to a similar fractionation on heparin-Sepharose (not shown).

Example 5

Expression of the hpa gene in various cell types, organs and tissues

Figure 12A:
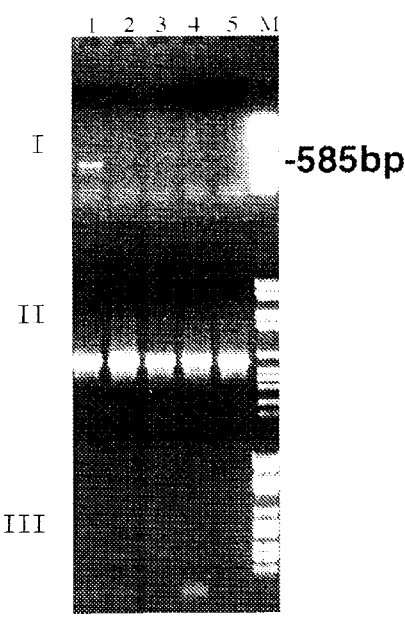
FIGS. 12a–e demonstrate expression of the hpa gene by RT-PCR with total RNA from human embryonal tissues (12a), human extra–embryonal tissues (12b) and cell lines from different origins (12c–e). RT-PCR products using hpa specific primers (I), primers for GAPDII housekeeping gene (II). and control reactions without reverse transcriptase demonstrating absence of genomic DNA or other contamination in RNA samples (III). M-DNA molecular weight marker VI (Bioehringer Mannheim). For 12a: lane 1—neutrophil cells (adult), lane 2—muscle, lane 3—thymus, lane 4—heart, lane 5—adrenal. For 12b: lane 1—kidney, lane 2—placenta (8 weeks). lane 3—placenta (11 weeks), lanes 4–7—mole (complete hydatidilorm mole), lane 8—cytotrophoblast cells (freshly isolated), lane 9—cytotrophoblast cells (1.5 h in vitro), lane 10—cytotrophoblast cells (6 h in vitro), lane 11—cytotrophoblast cells (18 h in vitro), lane 12—cytotrophoblast cells (48 h in vitro). For 12c: lane 1—JAR bladder cell line, lane 2—NCITT testicular tumor cell line, lane 3—SW-480 human hepatoma cell line, lane 4—HTR (cytotrophoblasts transformed by SV40), lane 5—HPTLP-I hepatocellular carcinoma cell line, lane 6—EJ-28 bladder carcinoma cell line. For 12d: lane 1—SK-Hep-1 human hepatoima cell line, lane 2—DAMI human megakaryocytic cell line, lane 3—DAMI cell line+PMA, lane 4—CHRF cell line+PMA, lane 5—CHRF cell line. For 12e: lane 1 ABAE bovine aortic endothelial cells, lane 2—1063 human ovarian cell line, lane 3—human breast carcinoma MDA435 cell line, lane 4—human breast carcinoma MDA231 cell line.
Figure 12B:
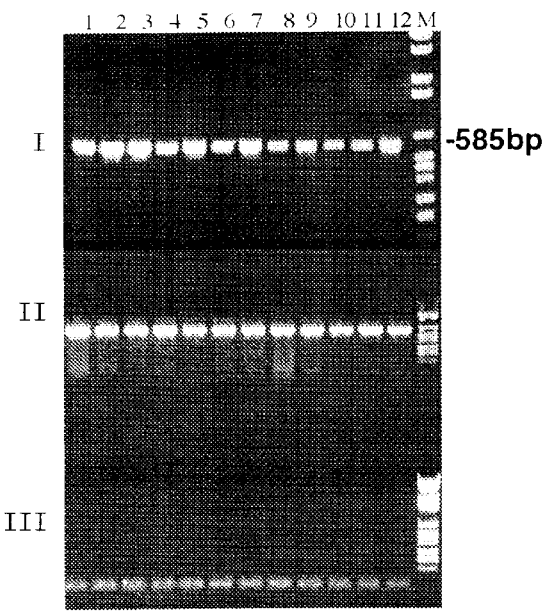
Figure 12C:
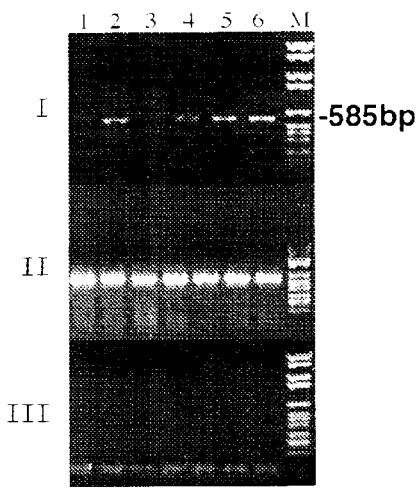
Figure 12D:
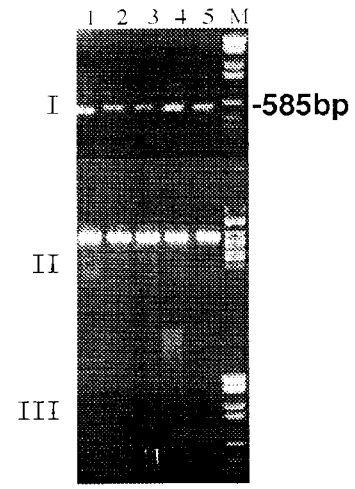
Figure 12E:
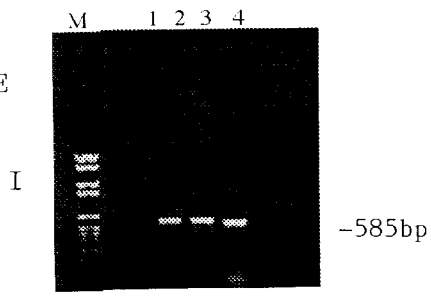

Referring now to FIGS. 12a–e, RT-PCR was applied to evaluate the expression of the hpa gene by various cell types and tissues. For this purpose, total RNA was reverse transcribed and amplified. The expected 585 bp long cDNA was clearly demonstrated in human kidney, placenta (8 and 11 weeks) and mole tissues, as well as in freshly isolated and short termed (1.5–48 h) cultured human placental cytotrophoblastic cells (FIG. 12a), all known to express a high heparanase activity (41). The hpa transcript was also expressed by normal human neutrophils (FIG. 12b). In contrast, there was no detectable expression of the hpa mRNA in embryonic human muscle tissue, thymus, heart and adrenal (FIG. 12b). The Spa gene was expressed by several, but not all, human bladder carcinoma cell lines (FIG. 12c), SK hepatoma (SK-Hep-1), ovarian carcinoma (OV 1063). breast carcinoma (435, 231), melanoma and megakaryocytic (DAMI, CHRF) human cell lines (FIGS. 12d–c).

The above described expression pattern of the hpa transcript was determined to be in a very good correlation with heparanase activity levels determined in various tissues and cell types (not shown).

Example 6 hpa homologous genes

EST databases were screened for sequences homologous to the hpa gene. Three mouse ESTs were identified (accession No. Aa177901, from mouse spleen, AaO67997 from mouse skin, Aa47943 from mouse embryo), assembled into a 824 bp cDNA fragment which contains a partial open reading frame (lacking a 5' end) of 629 bp and a 3' untranslated region of 195 bp (SEQ ID NO: 12). As shown in FIG. 13, the coding region is 80% similar to the 3' end of the hpa cDNA sequence. These ESTs are probably cDNA fragments of the mouse hpa homolog that encodes for the mouse heparanase.

Searching for consensus protein domains revealed an amino terminal homology between the heparanase and several precursor proteins such as Procollagen Alpha 1 precursor, Tyrosine-protein kinase-RYK, Fibulin-1, Insulin-like growth factor binding protein and several others. The amino terminus is highly hydrophobic and contains a potential trans-membrane domain. The homology to known signal peptide sequences suggests that it could function as a signal peptide for protein localization.

While the invention has been described with respect to a limited number of embodiments, it will be appreciated that many variations, modifications and other applications of the invention may be made.

LIST OF REFERENCES CITED HEREINABOVE BY NUMBERS

1. Wight, T. N., Kinsella, M. G., and Qwarnistromn, E. E. (1992). The role of proteoglycans in cell adhesion, migration and proliferation. *Curr. Opin. Cell Biol.*, 4, 793–801.

2. Jackson, R. L., Busch, S. J., and Cardin, A. L,. (1991). Glycosaminoglycans: Molecular properties, protein interactions and role in physiological processes. *Physiol. Rev.*, 71, 481–539.

3. Wight, T. N. (1989). Cell biology of arterial proteoglycans. *Arteriosclerosis*, 9, 1–20.

4. Kjellen, L,. and Lindahl, U. (1991). Protcoglycans: structures and interactions. *Annu. Rev. Biochem.*, 60, 443–475.

5. Ruoslahti, E., and Yamaguchi, Y. (1991). Proteoglycans as modulators of growth factor activities. *Cell*, 64, 867–869.

6. Vlodavsky, I., Eldor, A., Haimovitz-Friedman, A. Matzner, Y., Ishai-Michaeli, R., Levi, E., Bashkin, P., lider, O., Naparstek. Y. Cohen, I. R., and Fuks, Z. (1992). Expression of heparanase by platelets and circulating cells of the immune system: Possible involvement in diapedesis and extravasation. *Invasion & Metastasis*, 12, 112–127.

7. Vlodavsky, I., Mohsen, M., Lider, O., Ishai-Michaeli, R. Ekre, H.-P., Svahn, C. M., Vigoda, M., and Peretz, 1. (1995). Inhibition of tumor metastasis by heparanase inhibiting species of heparin. *Invasion & Metastasis*, 14, 290–302.

8. Nakajima, M., Irimura, T., and Nicolson, G. L. (1988). Heparanase and tumor metastasis. *J. Cell. Biochem.*, 36, 157–167.

9. Nicolson, G. L. (1988). Organ specificity of tumor metastasis: Role of preferential adhesion, invasion and growth of malignant cells at specific secondary sites. *Cancer Met. Rev.*, 7, 143–188.

10. Liotta, L. A., Rao, C. N., and Barsky, S. H. (1983). Tumor invasion and the extracellular matrix. *Lab. Invest.*, 49, 639–649.

11. Vlodavsky, I., Fuks Z., Bar-Ner, M., Ariav, Y., and Schirrmacher, V. (1983). Lymphoma cell mediated degradation of sulfated proteoglycans in the subendothelial extracellular matrix: Relationship to tumor cell metastasis. *Cancer Res.*, 43, 2704–2711.

12. Vlodavsky, I., Ishai-Michaeli, R., Bar-Ner, M., Fridman, R., Horowitz, A. T., Fuks, Z. and Biran, S. (1988). Involvement of heparanase in tumor metastasis and angiogenesis. Is. *J Med.*, 24, 464–470.

13. Vlodavsky, I., Liu, G. M. and Gospodarowicz. D. (1980). Morphological appearance, growth behavior and migratory activity of human tumor cells maintained on extracellular matrix vs. plastic. *Cell*, 19, 607–616.

14. Gospodarowicz, D., Delgado, D., and Vlodavsky, I. (1980). Permissive effect of the extracellular matrix on cell proliferation in-vitro. *Proc. Natl. Acac. Sci. USA.*, 77, 4094–4098.

15. Bashkin, P., Doctrow. S., Klagsbrun, M., Svahn. C. M. Folkman, J., and Vlodavsky, I. (1989). Basic fibroblast growth factor binds to subendothelial extracellular matrix and is released by heparitinase and heparin-like molecules. *Biochemistry*, 28, 1737–1743.

16. Parish, C. R., Coombe. D. R., Jakobsen, K. B., and Underwood, P. A. (1987). Evidence that sulphated polysaccharides inhibit tumor metastasis by blocking tumor cell-derived heparanase. *Int. J Cancer*, 40, 5 11–517.

16a. Vlodavsky, I., Hua-Quan Miao., Benezra, M., Lider, O., Bar-Shavit, R., Schmidt, A., and Peretz, T. (1997). Involvement of the extracellular matrix, heparan sulfate proteoglycans and heparan sulfate degrading enzymes in anigiogenesis and metastasis. In: Tumor Angiogenesis. Eds. C. E. Lewis, R. Bicknell & N. Ferrara. Oxford University Press, Oxford UK, pp. 125–140.

17. Burgess, W. H. and Maciag, T. (1989). The heparin-binding (fibroblast) growth factor family of proteins. *Annu. Rev. Biochein.*, 58, 575–606.

18. Folkman, J., and Klagsbrun, M. (1987). Angiogenic factors. *Science*, 235, 442–447.

19. Vlodavsky, I., 1Folkman, J., Sullivan, R., Fridman, R., Ishai-Michaelli, R., Sasse, J., and Klagsbrun, M. (1987). Endothelial cell-derived basic fibroblast growth factor: Synthesis and deposition into subendothelial extracellular matrix. *Proc. Natl. Acad. Sci. USA*, 84, 2292–2296.

20. Folkman, J., Klagsbrun, M., Sasse, J., Wadzinski, M., Ingber, D., and Vlodavsky, I. (1980). A heparin-binding angiogenic protein—basic fibroblast growth factor—is stored within basement membrane. *Am. J. Pathol.*, 130, 393400.

21. Cardon-Cardo, C., Vlodavsky, I., Haimovitz-Friedman, A., Hicklin, D., and Fuks, Z. (1990). Expression of basic fibroblast growth factor in normal human tissues. *Lab. Invest.*, 63, 832–840.

22. Ishai-Michaeli, R., Svahn C.-M., Chajek-Shaul, F. Korner, G., Ekre, H.-P., and Vlodavsky, I. (1992). Importance of size and sulfation of heparin in release of basic fibroblast factor from the vascular endothelium and extracellular matrix. *Biochemistry*, 31, 2080–2088.

23. Ishai-Michaeli, R., Eldor A., and Vlodavsky, I. (1990). Heparanase activity expressed by platelets, neutrophils and lymphoma cells releases active fibroblast growth factor from extracellular matrix. *Cell Reg.*, 1, 833–842.

24. Vlodavsky, I., Bar-Shavit, R., Ishai-Michaeli, R., Bashkin, P., and Fuks, Z. (1991). Extracellular sequestration and release of fibroblast growth factor: a regulatory mechanism? *Trends Biochem. Sci.*, 16, 268–271.

25. Vlodavsky, I., Bar-Shavit, R., Korner, (i., and Fuks, Z. (1993). Extracellular matrix-bound growth factors, enzymes and plasma proteins. In Basement membranes: Cellular and molecular aspects (eds. D. H. Rohrbach and R. Timpl), pp327–343. Academic press Inc., Orlando, Fla.

26. Yayon, A., Klagsbrun, M., Esko, J. D., leder, P., and Ornitz, D. M. (1991). Cell surface, heparin-like molecules are required for binding of basic fibroblast growth factor to its high affinity receptor. *Cell*, 64, 841–848.

27. Spivak-Kroizman, T., Lemmon, M. A., Dikic, I., Ladbury J. E., Pinchasi, D., Huang, J., Jaye, M., Crumley, G., Schliessinger, J., and Lax, I. (1994). Heparin-induced oligomerization of FGF molecules is responsible for FGF receptor dimerization, activation, and cell proliferation. *Cell*, 79, 1015–1024.

28. Ornitz, D. M., lerr, A. B., Nilsson, M., West. a., J., Svahn, C.-M., and Waksman, G. (1995). FGF binding and FGF receptor activation by synthetic heparan-derived di- and trisaccharides. *Science*, 268, 432–436.

29. Gitay-Goren, H., Soker, S. Vlodavsky, I., and Neufeld, G. (1992). Cell surface associated heparin-like molecules are required for the binding of vascular endothelial growth factor (VEGF) to its cell surface receptors. *J. Biol. Chem.*, 267, 6093–6098.

30. Lider, O., Baharav, E., Mekori, Y., Miller, T., Naparstek, Y., Vlodavsky, I., and Cohen, I. R. (1989). Suppression of experimental autoimmune diseases and prolongation of allograft survival by treatment of animals with heparinoid inhibitors of T lymphocyte heparanase. *J. Clin. Invest.*, 83, 752–756.

31. Lider, O., Cahalon, I,., Gilat, D., Hershkovitz, R., Siegel, D., Margalit, R., Shoseyov, O., and Cohn, I. R. (1995). A disaccharide that inhibits tumor necrosis factor α is formed from the extracellular matrix by the enzyme heparanase. *Proc. Natl. Acad. Sci. USA.*, 92, 5037–5041.

31a. Rapraeger, A., Krufka, A., and Olwin, B. R. (1991). Requirement of heparan sulfate for bFGF-mediated fibroblast growth and myoblast differentiation. *Science*, 252, 1705–1708.

32. Eisenberg, S., Sehayek, E., Olivecrona, T. and Vlodavsky, I. (1992). Lipoprotein lipase enhances binding of lipoproteins to heparan sulfate on cell surfaces and extracellular matrix. *J. Clin. Invest.*, 90, 20 13–2021.

33. Shieh, M-T., Wundunn, D., Montgomery, R. I., Esko, J. D., and Spear, P. G. J. (1992). Cell surface receptors for herpes simplex virus arc heparan sulfate proteoglycans. *J Cell Biol.*, 116, 1273–1281.

33a. Chen, Y., Maguire, T., Hileman, R. E., fromm, J. R., Esko, J. D., Linhardt, R. J., and Marks, R. M. (1997). Dengue virus infectivity depends on envelope protein binding to target cell heparan sulfate. *Nature Medicine* 3, 866871.

33b. Putnak. J. R., Kanesa-Thlasan, N., and Innis, B. L. (1997). A putative cellular receptor for dengue viruses. *Nature Medicine* 3, 828–829.

34. Narindrasorasak, S., Lowery, D., Gonzalez-DeWhitt. P., Poorman. R. A., Greenberg, B., Kisilevsky, R. (1991). High affinity interactions between the Alzheimer's beta-amyloid precursor protein and the basement membrane form of theparan sulfate proteoglycan. *J. Biol. Chem.*, 266, 12878–83.

35. Ross, R. (1993). The pathogenesis of atherosclerosis: a perspective for the 1990s. *Nature (Lond.).*, 362:801–809.

36. Zhong-Sheng, J., Walter, J., Brecht, R., Miranda, D. Mahmood Hussain. M., Innerarity, T. L. and Mahley, W. R. (1993). Role of heparan sulfate proteoglycans in the binding and uptake of apolipoprotein E-enriched remnant lipoproteins by cultured cells. *J. Biol. Chem.*, 268, 10160–10167.

37. Ernst, S., Langer, R., Cooney, Ch.L., and Sasiseklharan, R. (1995). Enzymatic degradation of glycosaminoglycans. Critical Reviews in Biochemistry and Molecular Biology, 30(5), 387–444.

38. Gospodarowicz, D., Mescher, A. L. Birdwell, C. R. (1977). Stimulation of corneal endothelial cell proliferation in vitro by fibroblast and epidermal growth factors. *Exp Eye Res* 25, 75–89.

39. Haimovitz-Friedman, A., Falcone, D. J., Eldor, A., Schirrmacher, V., Vlodavsky, I., and Fuks, Z. (1991) Activation of platelet heparitinase by tumor cell-derived factors. *Blood*, 78, 789–796.

39a. Savitsky, K., Platzer, M., Uziel, T., Gilad, S., Sartiel, A., Rosental, A., Elroy-Stein. O., Siloh, Y. and Rotman, G. (1997). Ataxia-telanigiectasia: structural diversity of untranslated sequences suggests complex post-translational regulation of ATM gene expression. Nucleic Acids Res. 25(9), 1678–1684.

40. Bar-Ner, M., EIdor, A., Wasserman, L., Matzner, Y., and Vlodavsky, I. (1987). Inhibition of heparanase mediated degradation of extracellular matrix heparan sulfate by modified and non-anticoagulant heparin species. *Blood*, 70, 551–557.

41. Goshen, R., Hochberg, A., Korner, G., Levi, E., Ishai-Michaeli, R., Elkin, M., de Grot, N., and Vlodavsky, I. (1996). Purification and characterization of placental heparanase and its expression by cultured cytotrophoblasts. *Mol. Human Reprod.* 2, 679–684.

What is claimed is:

1. A polynucleotide fragment comprising a polynucleotide sequence encoding a polypeptide having heparanase catalytic activity, wherein said polypeptide shares 70% homology with SEQ ID NO:10, as determined using default parameters of a DNA sequence analysis software package developed by the Genetic Computer Group (GCG) at the University of Wisconsin.

2. The polynucleotide fragment of claim 1, wherein said polynucleotide sequence includes nucleotides 63–1691 of SEQ ID NO:9.

3. The polynucleotide fragment of claim 1, wherein said polynucleotide sequence includes nucleotides 63–721 of SEQ ID NO:9.

4. The polynucleotide fragment of claim 1, wherein said polynucleotide is as set forth in SEQ ID NO:9.

5. The polynucleotide fragment of claim 1, wherein said polynucleotide sequence includes a segment of SEQ ID NO:9, said segment encodes said polypeptide having said heparanase catalytic activity.

6. The polynucleotide fragment of claim 1, wherein said polypeptide includes an amino acid sequence as set forth in SEQ ID NO:10.

7. The polynucleotide fragment of claim 1, wherein said polypeptide includes a segment of SEQ ID NO:10, said segment harbors said heparanase catalytic activity.

8. The polynucleotide fragment of claim 1, wherein said polynucleotide sequence is selected from the group consisting of double stranded DNA, single stranded DNA and RNA.

9. A polynucleotide sequence as set forth in SEQ D NO:9.

10. A polynucleotide sequence at least 70% homologous to SEQ ID NO:9, as determined using default parameters of a DNA sequence analysis software package developed by the Genetic Computer Group (GCG) at the University of Wisconsin, wherein said polynucleotide sequence encodes a polypeptide having heparanase catalytic activity.

11. A vector comprising a polynucleotide sequence encoding a polypeptide having heparanase catalytic activity, wherein said polypeptide shares 70% homology with SEQ ID NO:10, as determined using default parameters of a DNA sequence analysis software package developed by the Genetic Computer Group (GCG) at the University of Wisconsin.

12. The vector of claim 11, wherein said polynucleotide sequence includes nucleotides 63–1691 of SEQ ID NO:9.

13. The vector of claim 11, wherein said polynucleotide sequence includes nucleotides 63–721 of SEQ ID NO:9.

14. The vector of claim 11, wherein said polynucleotide sequence is as set forth in SEQ ID NO:9.

15. The vector of claim 11, wherein said polynucleotide sequence includes a segment of SEQ ID NO:9, said segment encodes said polypeptide having said heparanase catalytic activity.

16. While vector of claim 11, wherein said polypeptide includes an amino acid sequence as set forth in SEQ ID NO:10.

17. The vector of claim 11, wherein said polypeptide includes a segment of SEQ ID NO:10, said segment harbors said heparanase catalytic activity.

18. The vector of claim 11, wherein said polynucleotide sequence is selected from the group consisting of double stranded DNA, single stranded DNA and RNA.

19. The vector of claim 11, wherein said vector is a baculovirus vector.

20. A host cell comprising an exogenous polynucleotide fragment including a polynucleotide sequence encoding a polypeptide having heparanase catalytic activity, wherein said polypeptide shares 70% homology with SEQ ID NO:10 as determined using default parameters of a DNA sequence analysis software package developed by the Genetic Computer Group (GCG) at the University of Wisconsin.

21. The host cell of claim 20, wherein said polynucleotide sequence includes nucleotides 63–1691 of SEQ ID NO:9.

22. The host cell of claim 20, wherein said polynucleotide sequence includes nucleotides 63–721 of SEQ ID NO:9.

23. The host cell of claim 20, wherein said polynucleotide sequence is as set forth in SEQ ID NO:9.

24. The host cell of claim 20, wherein said polynucleotide sequence includes a segment of SEQ ID NO:9, said segment encodes said polypeptide having said heparanase catalytic activity.

25. The host cell of claim 20, wherein said polypeptide includes an amino acid sequence as set forth in SEQ ID NO:10.

26. The host cell of claim 20, wherein said polypeptide includes a segment of SEQ ID NO:10, said segment harbors said heparanase catalytic activity.

27. The host cell of claim 20, wherein said polynucleotide sequence is selected from the group consisting of double stranded DNA, single stranded DNA and RNA.

28. A host cell expressing a recombinant heparanase, wherein said recombinant heparanase shares 70% homology with SEQ ID NO:10, as determined using default parameter of a DNA sequence analysis software package developed by the Genetic Computer (Group (GCG) at the University of Wisconsin.

29. A heparanase overexpression system comprising a cell overexpressing heparanase catalytic activity, wherein said heparanase catalytic activity is effected by a recombinant heparanase sharing 7% homology with SEQ ID NO:10, as determined using default parameters of a DNA sequence analysis software package developed by the Genetic Computer Group (GCG) at the University of Wisconsin.

30. The host cell of claim 20, wherein said cell is an insect cell.

\* \* \* \* \*

UNITED STATES PATENT AND TRADEMARK OFFICE
CERTIFICATE OF CORRECTION

PATENT NO.   : 5,968,822
DATED        : October 19, 1999
INVENTOR(S)  : Pecker et al.

Page 1 of 1

It is certified that error appears in the above-identified patent and that said Letters Patent is hereby corrected as shown below:

Drawings,
Fig. 1, add line at bottom of page, as follows:

1681: CTGCTTGCATCTCTGAAAATAAAATATACTAGTCCTGACACTG
           A   C    I

Column 35,
Line 47, insert -- at least -- before "70%".

Column 36,
Line 57, insert -- at least -- before "70%".

Column 37,
Line 5, change "while" to "The".
Line 19, insert -- at least -- before "70%".

Column 38,
Line 14, insert -- at least -- before "70%".
Line 22, insert -- at least -- after "sharing" and change "7%" to -- 70% --.

Signed and Sealed this

Twenty-fifth Day of November, 2003

JAMES E. ROGAN
*Director of the United States Patent and Trademark Office*

SEQUENCE LISTING (1) GENERAL INFORMATION:

(iii) NUMBER OF SEQUENCES:12

(2) INFORMATION FOR SEQ ID NO:1:

(i) SEQUENCE CHARACTERISTICS:
      (A) LENGTH:27
      (B) TYPE:nucleic acid
      (C) STRANDEDNESS:single
      (D) TOPOLOGY:linear (xi) SEQUENCE DESCRIPTION: SEQ ID NO:1:

CCATCCTAAT ACGACTCACT ATAGGGC      27

(2) INFORMATION FOR SEQ ID NO:2:

(i) SEQUENCE CHARACTERISTICS:
      (A) LENGTH:24
      (B) TYPE:nucleic acid
      (C) STRANDEDNESS:single
      (D) TOPOLOGY:linear (xi) SEQUENCE DESCRIPTION: SEQ ID NO:2:

GTAGTGATGC CATGTAACTG AATC      24

(2) INFORMATION FOR SEQ ID NO:3:

(i) SEQUENCE CHARACTERISTICS:

(A) LENGTH:23
            (B) TYPE:nucleic acid
            (C) STRANDEDNESS:single
            (D) TOPOLOGY:linear (xi) SEQUENCE DESCRIPTION: SEQ ID NO:3:

ACTCACTATA GGGCTCGAGC GGC                                              23

(2) INFORMATION FOR SEQ ID NO:4:

(i) SEQUENCE CHARACTERISTICS:
            (A) LENGTH:22
            (B) TYPE:nucleic acid
            (C) STRANDEDNESS:single
            (D) TOPOLOGY:linear (xi) SEQUENCE DESCRIPTION: SEQ ID NO:4:

GCATCTTAGC CGTCTTTCTT CG                                               22

(2) INFORMATION FOR SEQ ID NO:5:

(i) SEQUENCE CHARACTERISTICS:
            (A) LENGTH:15
            (B) TYPE:nucleic acid
            (C) STRANDEDNESS:single
            (D) TOPOLOGY:linear (xi) SEQUENCE DESCRIPTION: SEQ ID NO:5:

TTTTTTTTTT TTTTT                                                       15

(2) INFORMATION FOR SEQ ID NO:6:

(i) SEQUENCE CHARACTERISTICS:
            (A) LENGTH:23
            (B) TYPE:nucleic acid
            (C) STRANDEDNESS:single
            (D) TOPOLOGY:linear (xi) SEQUENCE DESCRIPTION: SEQ ID NO:6:

TTCGATCCCA AGAAGGAATC AAC                                              23

(2) INFORMATION FOR SEQ ID NO:7:

(i) SEQUENCE CHARACTERISTICS:
            (A) LENGTH:24
            (B) TYPE:nucleic acid
            (C) STRANDEDNESS:single
            (D) TOPOLOGY:linear (xi) SEQUENCE DESCRIPTION: SEQ ID NO:7:

GTAGTGATGC CATGTAACTG AATC                                             24

(2) INFORMATION FOR SEQ ID NO:8:

(i) SEQUENCE CHARACTERISTICS:
            (A) LENGTH:9
            (B) TYPE:amino acid
            (C) STRANDEDNESS:single
            (D) TOPOLOGY:linear (xi) SEQUENCE DESCRIPTION: SEQ ID NO:8:

Tyr Gly Pro Asp Val Gly Gln Pro Arg
                 5                   9

(2) INFORMATION FOR SEQ ID NO:9:

(i) SEQUENCE CHARACTERISTICS:
            (A) LENGTH:1721

(B) TYPE:nucleic acid
        (C) STRANDEDNESS:double
        (D) TOPOLOGY:linear (xi) SEQUENCE DESCRIPTION: SEQ ID NO:9:

```
CTAGAGCTTT CGACTCTCCG CTGCGCGGCA GCTGGCGGGG GGAGCAGCCA GGTGAGCCCA      60

AGATGCTGCT GCGCTCGAAG CCTGCGCTGC CGCCGCCGCT GATGCTGCTG CTCCTGGGGC     120

CGCTGGGTCC CCTCTCCCCT GGCGCCCTGC CCCGACCTGC GCAAGCACAG GACGTCGTGG     180

ACCTGGACTT cTTCACCCAG GAGCCGCTGC ACCTGGTGAG CCCCTCGTTC CTGTCCGTCA     240

CCATTGACGC CAACCTGGCC ACGGACCCGC GGTTCCTCAT CCTCCTGGGT TCTCCAAAGC     300

TTCGTACCTT GGCCAGAGGC TTGTCTCCTG CGTACCTGAG GTTTGGTGGC ACCAAGACAG     360

ACTTCCTAAT TTTCGATCCC AAGAAGGAAT CAACCTTTGA AGAGAGAAGT TACTGGCAAT     420

CTCAAGTCAA CCAGGATATT TGCAAATATG GATCCATCCC TCCTGATGTG GAGGAGAAGT     480

TACGGTTGGA ATGGCCCTAC CAGGAGCAAT TGCTACTCCG AGAACACTAC CAGAAAAAGT     540

TCAAGAACAG CACCTACTCA AGAAGCTCTG TAGATGTGCT ATACACTTTT GCAAACTGCT     600

CAGGACTGGA CTTGATCTTT GGCCTAAATG CGTTATTAAG AACAGCAGAT TTGCAGTGGA     660

ACAGTTCTAA TGCTCAGTTG CTCCTGGACT ACTGCTCTTC CAAGGGGTAT AACATTTCTT     720

GGGAACTAGG CAATGAACCT AACAGTTTCC TTAAGAAGGC TGATATTTTC ATCAATGGGT     780

CGCAGTTAGG AGAAGATTAT ATTCAATTGC ATAAACTTCT AAGAAAGTCC ACCTTCAAAA     840

ATGCAAAACT CTATGGTCCT GATGTTGGTC AGCCTCGAAG AAAGACGGCT AAGATGCTGA     900

AGAGCTTCCT GAAGGCTGGT GGAGAAGTGA TTGATTCAGT TACATGGCAT CACTACTATT     960

TGAATGGACG GACTGCTACC AGGGAAGATT TTCTAAACCC TGATGTATTG GACATTTTTA    1020

TTTCATCTGT GCAAAAAGTT TTCCAGGTGG TTGAGAGCAC CAGGCCTGGC AAGAAGGTCT    1080

GGTTAGGAGA AACAAGCTCT GCATATGGAG GCGGAGCGCC CTTGCTATCC GACACCTTTG    1140

CAGCTGGCTT TATGTGGCTG GATAAATTGG GCCTGTCAGC CCGAATGGGA ATAGAAGTGG    1200

TGATGAGGCA AGTATTCTTT GGAGCAGGAA ACTACCATTT AGTGGATGAA AACTTCGATC    1260

CTTTACCTGA TTATTGGCTA TCTCTTCTGT TCAAGAAATT GGTGGGCACC AAGGTGTTAA    1320

TGGCAAGCGT GCAAGGTTCA AAGAGAAGGA AGCTTCGAGT ATACCTTCAT TGCACAAACA    1380

CTGACAATCC AAGGTATAAA GAAGGAGATT TAACTCTGTA TGCCATAAAC CTCCATAACG    1440

TCACCAAGTA CTTGCGGTTA CCCTATCCTT TTTCTAACAA GCAAGTGGAT AAATACCTTC    1500

TAAGACCTTT GGGACCTCAT GGATTACTTT CCAAATCTGT CCAACTCAAT GGTCTAACTC    1560

TAAAGATGGT GGATGATCAA ACCTTGCCAC CTTTAATGGA AAAACCTCTC CGGCCAGGAA    1620

GTTCACTGGG CTTGCCAGCT TTCTCATATA GTTTTTTTGT GATAAGAAAT GCCAAAGTTG    1680

CTGCTTGCAT CTGAAAATAA AATATACTAG TCCTGACACT G                       1721
```

(2) INFORMATION FOR SEQ ID NO:10:

(i) SEQUENCE CHARACTERISTICS:
        (A) LENGTH:543
        (B) TYPE:amino acid
        (C) STRANDEDNESS:single
        (D) TOPOLOGY:linear (xi) SEQUENCE DESCRIPTION: SEQ ID NO:10:

```
Met Leu Leu Arg Ser Lys Pro Ala Leu Pro Pro Leu Met Leu Leu
              5                  10                  15

Leu Leu Gly Pro Leu Gly Pro Leu Ser Pro Gly Ala Leu Pro Arg Pro
             20                  25                  30
```

```
Ala Gln Ala Gln Asp Val Val Asp Leu Asp Phe Phe Thr Gln Glu Pro
         35                  40                  45

Leu His Leu Val Ser Pro Ser Phe Leu Ser Val Thr Ile Asp Ala Asn
         50                  55                  60

Leu Ala Thr Asp Pro Arg Phe Leu Ile Leu Leu Gly Ser Pro Lys Leu
 65              70                  75                      80

Arg Thr Leu Ala Arg Gly Leu Ser Pro Ala Tyr Leu Arg Phe Gly Gly
                 85                  90                  95

Thr Lys Thr Asp Phe Leu Ile Phe Asp Pro Lys Lys Glu Ser Thr Phe
            100                 105                 110

Glu Glu Arg Ser Tyr Trp Gln Ser Gln Val Asn Gln Asp Ile Cys Lys
        115                 120                 125

Tyr Gly Ser Ile Pro Pro Asp Val Glu Glu Lys Leu Arg Leu Glu Trp
        130                 135                 140

Pro Tyr Gln Glu Gln Leu Leu Leu Arg Glu His Tyr Gln Lys Lys Phe
145                 150                 155                 160

Lys Asn Ser Thr Tyr Ser Arg Ser Ser Val Asp Val Leu Tyr Thr Phe
                165                 170                 175

Ala Asn Cys Ser Gly Leu Asp Leu Ile Phe Gly Leu Asn Ala Leu Leu
            180                 185                 190

Arg Thr Ala Asp Leu Gln Trp Asn Ser Ser Asn Ala Gln Leu Leu Leu
        195                 200                 205

Asp Tyr Cys Ser Ser Lys Gly Tyr Asn Ile Ser Trp Glu Leu Gly Asn
        210                 215                 220

Glu Pro Asn Ser Phe Leu Lys Lys Ala Asp Ile Phe Ile Asn Gly Ser
225                 230                 235                 240

Gln Leu Gly Glu Asp Tyr Ile Gln Leu His Lys Leu Leu Arg Lys Ser
                245                 250                 255

Thr Phe Lys Asn Ala Lys Leu Tyr Gly Pro Asp Val Gly Gln Pro Arg
            260                 265                 270

Arg Lys Thr Ala Lys Met Leu Lys Ser Phe Leu Lys Ala Gly Gly Glu
        275                 280                 285

Val Ile Asp Ser Val Thr Trp His His Tyr Tyr Leu Asn Gly Arg Thr
290                 295                 300

Ala Thr Arg Glu Asp Phe Leu Asn Pro Asp Val Leu Asp Ile Phe Ile
305                 310                 315                 320

Ser Ser Val Gln Lys Val Phe Gln Val Val Glu Ser Thr Arg Pro Gly
                325                 330                 335

Lys Lys Val Trp Leu Gly Glu Thr Ser Ser Ala Tyr Gly Gly Gly Ala
            340                 345                 350

Pro Leu Leu Ser Asp Thr Phe Ala Ala Gly Phe Met Trp Leu Asp Lys
        355                 360                 365

Leu Gly Leu Ser Ala Arg Met Gly Ile Glu Val Val Met Arg Gln Val
        370                 375                 380

Phe Phe Gly Ala Gly Asn Tyr His Leu Val Asp Glu Asn Phe Asp Pro
385                 390                 395                 400

Leu Pro Asp Tyr Trp Leu Ser Leu Leu Phe Lys Lys Leu Val Gly Thr
                405                 410                 415

Lys Val Leu Met Ala Ser Val Gln Gly Ser Lys Arg Arg Lys Leu Arg
            420                 425                 430

Val Tyr Leu His Cys Thr Asn Thr Asp Asn Pro Arg Tyr Lys Glu Gly
        435                 440                 445

Asp Leu Thr Leu Tyr Ala Ile Asn Leu His Asn Val Thr Lys Tyr Leu
```

```
                           450                455                460
     Arg Leu Pro Tyr Pro Phe Ser Asn Lys Gln Val Asp Lys Tyr Leu Leu
     465                470                475                480

Arg Pro Leu Gly Pro His Gly Leu Leu Ser Lys Ser Val Gln Leu Asn
                         485                490                495

Gly Leu Thr Leu Lys Met Val Asp Asp Gln Thr Leu Pro Pro Leu Met
                     500                505                510

Glu Lys Pro Leu Arg Pro Gly Ser Ser Leu Gly Leu Pro Ala Phe Ser
                 515                520                525

Tyr Ser Phe Phe Val Ile Arg Asn Ala Lys Val Ala Ala Cys Ile
             530                535                540     543

(2) INFORMATION FOR SEQ ID NO:11:

(i) SEQUENCE CHARACTERISTICS:
        (A) LENGTH:1721
        (B) TYPE:nucleic acid
        (C) STRANDEDNESS:double
        (D) TOPOLOGY:linear (xi) SEQUENCE DESCRIPTION: SEQ ID NO:11:

CT AGA GCT TTC GAC         14

TCT CCG CTG CGC GGC AGC TGG CGG GGG GAG CAG CCA GGT GAG CCC AAG         62

ATG CTG CTG CGC TCG AAG CCT GCG CTG CCG CCG CCG CTG ATG CTG CTG        110
Met Leu Leu Arg Ser Lys Pro Ala Leu Pro Pro Pro Leu Met Leu Leu
                  5                  10                 15

CTC CTG GGG CCG CTG GGT CCC CTC TCC CCT GGC GCC CTG CCC CGA CCT        158
Leu Leu Gly Pro Leu Gly Pro Leu Ser Pro Gly Ala Leu Pro Arg Pro
             20                  25                 30

GCG CAA GCA CAG GAC GTC GTG GAC CTG GAC TTC TTC ACC CAG GAG CCG        206
Ala Gln Ala Gln Asp Val Val Asp Leu Asp Phe Phe Thr Gln Glu Pro
         35                  40                  45

CTG CAC CTG GTG AGC CCC TCG TTC CTG TCC GTC ACC ATT GAC GCC AAC        254
Leu His Leu Val Ser Pro Ser Phe Leu Ser Val Thr Ile Asp Ala Asn
     50                  55                  60

CTG GCC ACG GAC CCG CGG TTC CTC ATC CTC CTG GGT TCT CCA AAG CTT        302
Leu Ala Thr Asp Pro Arg Phe Leu Ile Leu Leu Gly Ser Pro Lys Leu
 65                  70                  75                  80

CGT ACC TTG GCC AGA GGC TTG TCT CCT GCG TAC CTG AGG TTT GGT GGC        350
Arg Thr Leu Ala Arg Gly Leu Ser Pro Ala Tyr Leu Arg Phe Gly Gly
                 85                  90                  95

ACC AAG ACA GAC TTC CTA ATT TTC GAT CCC AAG AAG GAA TCA ACC TTT        398
Thr Lys Thr Asp Phe Leu Ile Phe Asp Pro Lys Lys Glu Ser Thr Phe
            100                 105                 110

GAA GAG AGA AGT TAC TGG CAA TCT CAA GTC AAC CAG GAT ATT TGC AAA        446
Glu Glu Arg Ser Tyr Trp Gln Ser Gln Val Asn Gln Asp Ile Cys Lys
        115                 120                 125

TAT GGA TCC ATC CCT CCT GAT GTG GAG GAG AAG TTA CGG TTG GAA TGG        494
Tyr Gly Ser Ile Pro Pro Asp Val Glu Glu Lys Leu Arg Leu Glu Trp
    130                 135                 140

CCC TAC CAG GAG CAA TTG CTA CTC CGA GAA CAC TAC CAG AAA AAG TTC        542
Pro Tyr Gln Glu Gln Leu Leu Leu Arg Glu His Tyr Gln Lys Lys Phe
145                 150                 155                 160

AAG AAC AGC ACC TAC TCA AGA AGC TCT GTA GAT GTG CTA TAC ACT TTT        590
Lys Asn Ser Thr Tyr Ser Arg Ser Ser Val Asp Val Leu Tyr Thr Phe
                165                 170                 175

GCA AAC TGC TCA GGA CTG GAC TTG ATC TTT GGC CTA AAT GCG TTA TTA        638
Ala Asn Cys Ser Gly Leu Asp Leu Ile Phe Gly Leu Asn Ala Leu Leu
            180                 185                 190
```

```
AGA ACA GCA GAT TTG CAG TGG AAC AGT TCT AAT GCT CAG TTG CTC CTG       686
Arg Thr Ala Asp Leu Gln Trp Asn Ser Ser Asn Ala Gln Leu Leu Leu
            195                 200                 205

GAC TAC TGC TCT TCC AAG GGG TAT AAC ATT TCT TGG GAA CTA GGC AAT       734
Asp Tyr Cys Ser Ser Lys Gly Tyr Asn Ile Ser Trp Glu Leu Gly Asn
210                 215                 220

GAA CCT AAC AGT TTC CTT AAG AAG GCT GAT ATT TTC ATC AAT GGG TCG       782
Glu Pro Asn Ser Phe Leu Lys Lys Ala Asp Ile Phe Ile Asn Gly Ser
225                 230                 235                 240

CAG TTA GGA GAA GAT TAT ATT CAA TTG CAT AAA CTT CTA AGA AAG TCC       830
Gln Leu Gly Glu Asp Tyr Ile Gln Leu His Lys Leu Leu Arg Lys Ser
                245                 250                 255

ACC TTC AAA AAT GCA AAA CTC TAT GGT CCT GAT GTT GGT CAG CCT CGA       878
Thr Phe Lys Asn Ala Lys Leu Tyr Gly Pro Asp Val Gly Gln Pro Arg
            260                 265                 270

AGA AAG ACG GCT AAG ATG CTG AAG AGC TTC CTG AAG GCT GGT GGA GAA       926
Arg Lys Thr Ala Lys Met Leu Lys Ser Phe Leu Lys Ala Gly Gly Glu
        275                 280                 285

GTG ATT GAT TCA GTT ACA TGG CAT CAC TAC TAT TTG AAT GGA CGG ACT       974
Val Ile Asp Ser Val Thr Trp His His Tyr Tyr Leu Asn Gly Arg Thr
    290                 295                 300

GCT ACC AGG GAA GAT TTT CTA AAC CCT GAT GTA TTG GAC ATT TTT ATT      1022
Ala Thr Arg Glu Asp Phe Leu Asn Pro Asp Val Leu Asp Ile Phe Ile
305                 310                 315                 320

TCA TCT GTG CAA AAA GTT TTC CAG GTG GTT GAG AGC ACC AGG CCT GGC      1070
Ser Ser Val Gln Lys Val Phe Gln Val Val Glu Ser Thr Arg Pro Gly
                325                 330                 335

AAG AAG GTC TGG TTA GGA GAA ACA AGC TCT GCA TAT GGA GGC GGA GCG      1118
Lys Lys Val Trp Leu Gly Glu Thr Ser Ser Ala Tyr Gly Gly Gly Ala
            340                 345                 350

CCC TTG CTA TCC GAC ACC TTT GCA GCT GGC TTT ATG TGG CTG GAT AAA      1166
Pro Leu Leu Ser Asp Thr Phe Ala Ala Gly Phe Met Trp Leu Asp Lys
        355                 360                 365

TTG GGC CTG TCA GCC CGA ATG GGA ATA GAA GTG GTG ATG AGG CAA GTA      1214
Leu Gly Leu Ser Ala Arg Met Gly Ile Glu Val Val Met Arg Gln Val
    370                 375                 380

TTC TTT GGA GCA GGA AAC TAC CAT TTA GTG GAT GAA AAC TTC GAT CCT      1262
Phe Phe Gly Ala Gly Asn Tyr His Leu Val Asp Glu Asn Phe Asp Pro
385                 390                 395                 400

TTA CCT GAT TAT TGG CTA TCT CTT CTG TTC AAG AAA TTG GTG GGC ACC      1310
Leu Pro Asp Tyr Trp Leu Ser Leu Leu Phe Lys Lys Leu Val Gly Thr
                405                 410                 415

AAG GTG TTA ATG GCA AGC GTG CAA GGT TCA AAG AGA AGG AAG CTT CGA      1358
Lys Val Leu Met Ala Ser Val Gln Gly Ser Lys Arg Arg Lys Leu Arg
            420                 425                 430

GTA TAC CTT CAT TGC ACA AAC ACT GAC AAT CCA AGG TAT AAA GAA GGA      1406
Val Tyr Leu His Cys Thr Asn Thr Asp Asn Pro Arg Tyr Lys Glu Gly
        435                 440                 445

GAT TTA ACT CTG TAT GCC ATA AAC CTC CAT AAC GTC ACC AAG TAC TTG      1454
Asp Leu Thr Leu Tyr Ala Ile Asn Leu His Asn Val Thr Lys Tyr Leu
    450                 455                 460

CGG TTA CCC TAT CCT TTT TCT AAC AAG CAA GTG GAT AAA TAC CTT CTA      1502
Arg Leu Pro Tyr Pro Phe Ser Asn Lys Gln Val Asp Lys Tyr Leu Leu
465                 470                 475                 480

AGA CCT TTG GGA CCT CAT GGA TTA CTT TCC AAA TCT GTC CAA CTC AAT      1550
Arg Pro Leu Gly Pro His Gly Leu Leu Ser Lys Ser Val Gln Leu Asn
                485                 490                 495

GGT CTA ACT CTA AAG ATG GTG GAT GAT CAA ACC TTG CCA CCT TTA ATG      1598
Gly Leu Thr Leu Lys Met Val Asp Asp Gln Thr Leu Pro Pro Leu Met
            500                 505                 510
```

-continued

```
GAA AAA CCT CTC CGG CCA GGA AGT TCA CTG GGC TTG CCA GCT TTC TCA         1646
Glu Lys Pro Leu Arg Pro Gly Ser Ser Leu Gly Leu Pro Ala Phe Ser
        515                 520                 525

TAT AGT TTT TTT GTG ATA AGA AAT GCC AAA GTT GCT GCT TGC ATC TGA         1694
Tyr Ser Phe Phe Val Ile Arg Asn Ala Lys Val Ala Ala Cys Ile
    530                 535                 540         543

AAA TAA AAT ATA CTA GTC CTG ACA CTG                                     1721
```

(2) INFORMATION FOR SEQ ID NO:12:

(i) SEQUENCE CHARACTERISTICS:
        (A) LENGTH:824
        (B) TYPE:nucleic acid
        (C) STRANDEDNESS:double
        (D) TOPOLOGY:linear (xi) SEQUENCE DESCRIPTION: SEQ ID NO:12:

```
CTGGCAAGAA GGTCTGGTTG GGAGAGACGA GCTCAGCTTA CGGTGGCGGT GCACCCTTGC         60

TGTCCAACAC CTTTGCAGCT GGCTTTATGT GGCTGGATAA ATTGGGCCTG TCAGCCCAGA        120

TGGGCATAGA AGTCGTGATG AGGCAGGTGT TCTTCGGAGC AGGCAACTAC CACTTAGTGG        180

ATGAAAACTT TGAGCCTTTA CCTGATTACT GGCTCTCTCT TCTGTTCAAG AAACTGGTAG        240

GTCCCAGGGT GTTACTGTCA AGAGTGAAAG GCCCAGACAG GAGCAAACTC CGAGTGTATC        300

TCCACTGCAC TAACGTCTAT CACCCACGAT ATCAGGAAGG AGATCTAACT CTGTATGTCC        360

TGAACCTCCA TAATGTCACC AAGCACTTGA AGGTACCGCC TCCGTTGTTC AGGAAACCAG        420

TGGATACGTA CCTTCTGAAG CCTTCGGGGC CGGATGGATT ACTTTCCAAA TCTGTCCAAC        480

TGAACGGTCA AATTCTGAAG ATGGTGGATG AGCAGACCCT GCCAGCTTTG ACAGAAAAAC        540

CTCTCCCCGC AGGAAGTGCA CTAAGCCTGC CTGCCTTTTC CTATGGTTTT TTTGTCATAA        600

GAAATGCCAA AATCGCTGCT TGTATATGAA AATAAAAGGC ATACGGTACC CCTGAGACAA        660

AAGCCGAGGG GGGTGTTATT CATAAAACAA AACCCTAGTT TAGGAGGCCA CCTCCTTGCC        720

GAGTTCCAGA GCTTCGGGAG GGTGGGGTAC ACTTCAGTAT TACATTCAGT GTGGTGTTCT        780

CTCTAAGAAG AATACTGCAG GTGGTGACAG TTAATAGCAC TGTG                        824
```